United States Patent [19]
Whittaker et al.

[11] Patent Number: 5,840,974
[45] Date of Patent: Nov. 24, 1998

[54] METALLOPROTEINASE INHIBITORS

[75] Inventors: Mark Whittaker; Raymond Paul Beckett; Zoe Marie Spavold; Fionna Mitchell Martin, all of Oxford, United Kingdom

[73] Assignee: Britisch Biotech Pharmaceuticals, Ltd., England

[21] Appl. No.: 925,592

[22] Filed: Sep. 8, 1997

[30] Foreign Application Priority Data

Dec. 4, 1996 [GB] United Kingdom .................... 9625154
Jun. 27, 1997 [GB] United Kingdom .................... 9713472

[51] Int. Cl.$^6$ ...................... C07C 259/06; C07C 237/22; C07C 229/00
[52] U.S. Cl. ............................ 562/623; 562/621; 562/448
[58] Field of Search ..................................... 562/621, 623, 562/448

[56] References Cited

FOREIGN PATENT DOCUMENTS

| | | |
|---|---|---|
| 574758 | 12/1993 | European Pat. Off. . |
| 684240 | 11/1995 | European Pat. Off. . |
| WO 90/05719 | 5/1990 | WIPO . |
| WO 94/21625 | 9/1994 | WIPO . |
| WO 95/33731 | 12/1995 | WIPO . |
| WO 96/16027 | 5/1996 | WIPO . |
| WO 96/26918 | 9/1996 | WIPO . |

OTHER PUBLICATIONS

Abreo et al. poster entitled "Truncated Succinamide Hydroxamates with Nanomolar Potency against Various MMPs," 213th ACS Meeting in San Francisco, 13th–17th Apr. 1997.

Chapman, et al., "Inhibition of Matrix Metalloproteinases by N–Carboxyalkyl Peptides," J. Med. Chem., 36:4293–4301 (1993).

*Primary Examiner*—Gary Geist
*Assistant Examiner*—Brian J. Davis
*Attorney, Agent, or Firm*—Banner & Witcoff, Ltd.

[57] ABSTRACT

Compound of formula (I)

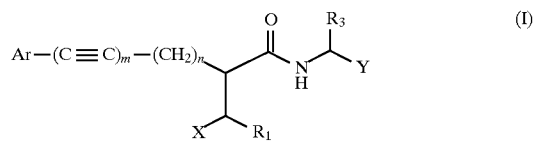

wherein Ar represents an optionally substituted phenyl or heteroaryl group, m is 1 or 2, n is 0, 1, 2, 3 or 4, X represents —COOH or —CONHOH and $R_1$, $R_3$ and Y are as defined in the specification, are inhibitors of metalloproteinases involved in tissue degradation.

24 Claims, No Drawings

METALLOPROTEINASE INHIBITORS

The present invention relates to therapeutically active compounds, to processes for their preparation, to pharmaceutical compositions containing them, and to the use of such compounds in medicine. In particular, the compounds are inhibitors of metalloproteinases involved in tissue degradation.

BACKGROUND TO THE INVENTION

The matrix metalloproteinases (MMPs) are a family of enzymes including interstitial collagenase, neutrophil collagenase, collagenase-3, 72kDa gelatinase, 92kDa gelatinase, stromelysin-1, stromelysin-2, stromelysin-3, matrilysin, macrophage metalloelastase, membrane-type metalloproteinase-1 and membrane-type metalloproteinase-2. These enzymes share a common zinc-containing catalytic domain and a pro-sequence which maintains latency. A wide range of cells and tissues can express MMPs in response to activation by inflammatory stimuli such as interleukin-1 or tumour necrosis factor-a (TNF-α). Different stimuli can induce overlapping yet distinct repertoires of MMPs and different cell types can respond to the same stimuli by expression of distinct combinations of MMPs. MMPs can attack the protein components of extracellular matrix such as collagens, vitronectin and elastin, and have recently been shown to process membrane proteins such as pro-TNF-α to release soluble TNF-α. MMPs are thought to play a central role in the pathology of inflammatory diseases such as rheumatoid arthritis as well as in the growth and metastasis of tumours.

Compounds which have the property of inhibiting the action of MMPs are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas.

Many known MMP inhibitors are peptide derivatives, based on naturally occurring amino acids, and are analogues of the cleavage site in the collagen molecule. Chapman et al (J. Med. Chem. 1993, 36, 4293–4301) report some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the active site zinc(ll) ion in the MMP, and known classes include those in which the zinc binding group is a hydroxamic acid, carboxylic acid, mercapto, and oxygenated phosphorus (eg. phosphinic acid and phosphonic acid) groups.

Two known classes of pseudopeptide or peptide mimetic MMP inhibitors have a hydroxamic acid group or a carboxylic group respectively as their zinc binding groups. Many such known MMPs may be represented by the structural formula (IA)

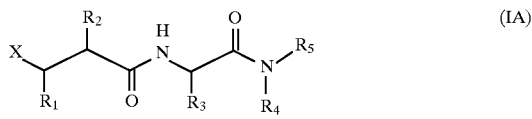

(IA)

in which X is the zinc binding hydroxamic acid (—CONHOH) or carboxylic acid (—COOH) group and the groups $R_1$ to $R_5$ are variable in accordance with the specific prior art disclosures of such compounds.

WO 96/16027 (Syntex/Agouron) discloses a class of MMP inhibitor compounds which can be represented by formula (IA) above. The principal structural characterising feature of the compounds disclosed in WO 96/16027 is the group $R_2$ which is defined in the publication as being a group $R^2$—X—wherein X is —$(CH_2)_m$—Y—$(CH_2)_n$, Y being O, S or a single bond, m and n being 0, 1, 2, 3 or 4 and m+n being 0,1, 2, 3, or 4, and $R^2$ being (inter alia) aryl or heteroaryl, the latter terms including biaryl such as biphenyl and heteroaryl-aryl such as 4-pyridylphenyl.

Another known class of collagenase inhibitors is represented by those disclosed in EP-A-0574758 (Roche), EP-A-0684240 (Roche), and WO 95/33731 (Roche). In general, the compounds disclosed in those publications may be represented by the structural formula (IB):

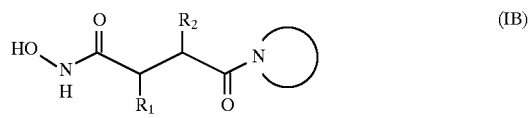

(IB)

in which $R_1$, $R_2$ and the N-containing ring are variable in accordance with the specific disclosures of the publications.

M. A. Abreo et al. presented a poster entitled "Truncated Succinamide Hydroxamates With Nanomolar Potency against various MMPs" at the 213th ACS Meeting in San Francisco, 13th–17th April 1997. In that poster compounds of formula (IC) were disclosed:

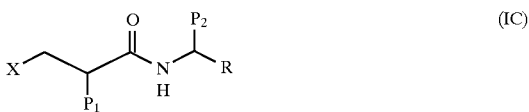

(IC)

wherein X is —COOH or —CONHOH, $P_1$ is biphenylpropyl, R is hydroxymethyl and $P_2$ is the side chain found in one of the following amino acids, namely serine, tert-butylglycine, histidine, O-benzylthreonine, phenylalanine, tyrosine, methionine, threonine, and 3-(3-pyridyl)alanine. Also disclosed were compounds of formula (IC) wherein X and $P_1$ are as just defined, and $P_2$ and R together with the carbon atom to which they are attached form a trans-cyclohexan-2-ol or glucosyl ring. The authors stated that the compound (IC), $P_2$ =the histidine side chain and R=hydroxymethyl, showed good plasma levels after iv and oral dosing to mice. They also stated that the X-ray crystal structure of compound (IC), $P_2$ =tert-butyl and R=hydroxymethyl, was obtained with stromelysin-1, and that the hydroxyl moiety in R makes an H-bond in the $P_3'$ area of the enzyme, while the tert-butyl group makes good hydrophobic contact in the P2' area.

BRIEF DESCRIPTION OF THE INVENTION

The present invention makes available a new class of MMP inhibitors which conform to the general formula (IA) or (IC) above. The compounds of the invention are principally distinguished from the compounds disclosed in WO 96/16027 and by Abreo et. al. (loc. cit.) by the identity of the group $R_2$ (formulae (IA) and (IC)), which in the present compounds contains one or two conformationally rigid triple bonds.

DETAILED DESCRIPTION OF THE INVENTION

The present invention provides compounds of formula (I)

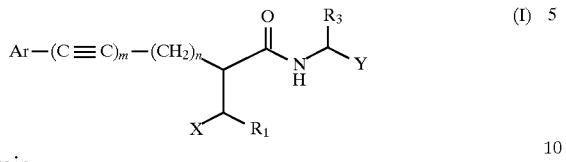

wherein

Ar represents an optionally substituted phenyl or heteroaryl group;

m is 1 or 2;

n is 0, 1, 2, 3 or 4;

x represents —COOH or —CONHOH;

$R_1$ represents hydrogen, $(C_1-C_6)$alkyl; $(C_3-C_8)$ cycloalkyl; $(C_2-C_6)$alkenyl; phenyl; substituted phenyl; phenyl $(C_1-C_6)$alkyl); substituted phenyl$(C_1-C_6)$ alkyl; heterocyclyl; substituted heterocyclyl; heterocyclyl$(C_1-C_6)$alkyl; substituted heterocyclyl $(C_1-C_6)$alkyl; amino; protected amino; acylamino; OH; SH; $(C_1-C_6)$alkoxy; $(C_1-C_6)$alkylamino; di-$(C_1-C_6)$ alkylamino; $(C_1-C_6)$alkylthio; amino$(C_1-C_6)$ alkyl; hydroxy$(C_1-C_6)$alkyl, mercapto$(C_1-C_6)$alkyl or carboxy$(C_1-C_6)$alkyl wherein the amino- , hydroxy- , mercapto- or carboxyl- group are optionally protected or the carboxyl- group amidated; lower alkyl substituted by carbamoyl, mono(lower alkyl)carbamoyl, di(lower alkyl)carbamoyl, di(lower alkyl)amino, or carboxy-lower alkanoylamino; or a group B'SO$_p$A'— wherein p is 0, 1 or 2 and B' is hydrogen or a $(C_1-C_6)$ alkyl, phenyl, substituted phenyl, heterocyclyl, $(C_1-C_6)$ acyl, phenacyl or substituted phenacyl group, and A' represents $(C_1-C_6)$alkyl;

$R_3$ represents the characterising group of a natural or non-natural α amino acid in which any functional groups may be protected;

Y Is a group of formula (ID) or (IE)

wherein:

$R_4$ represents (a) an optionally substituted cycloalkyl or cycloalkenyl ring; or (b) a phenyl or heteroaryl ring which may be fused to a benzene or heteroaryl ring, either or both of which rings may be substituted, and in which any ring nitrogen atom may be oxidised as an N-oxide, or (c) a groups —CHR$^x$R$^Y$ wherein R$^x$ and R$^y$ each independently represents an optionally substituted phenyl or heteroaryl ring which may be linked covalently to each other by a bond or by a $C_1-C_4$ alkylene or $C_2-C_4$ alkenylene bridge;

(d) a group of formula —(Z'—O)$_w$—Z wherein Z' is straight or branched $C_1-C_6$ alkyl optionally interrupted by one or more non-adjacent S and/or N atoms, w is an integer >1, and no continuous linear sequence of atoms in the group $R_4$ is >12, or (e) a straight or branched $C_1-C_6$ alkyl group, optionally interrupted by one or more non-adjacent S and/or N atoms, which is substituted by at least two substituents of formula —(Z'''$)_x$—(OZ)$_q$ wherein Z''' is straight or branched $C_1-C_6$ alkyl optionally interrupted by one or more non-adjacent S and/or N atoms, x is 0 or 1, q is 1 or 2, and no continuous linear sequence of atoms in the group $R_4$ is >12, or (f) hydrogen, $C_1-C_6$ alkyl, $C_1-C_4$ perfluoroalkyl, or a group D-($C_1-C_6$ alkyl)- wherein D is hydroxy, $C_1-C_6$ alkoxy, $C_1-C_6$ alkylthio, acylamino, optionally substituted phenyl or heteroaryl, $NH_2$, or mono- or di-($C_1-C_6$ alkyl)amino or N-morpholino;

or $R_3$ and $R_4$ taken together represent a divalent chain of formula —C(R$^a$)(R$^b$)—A''—Alk-wherein R$^a$ and R$^b$ are independently hydrogen or $C_1-C_6$ alkyl, A'' is a bond, —O—, —S—, —S—S—, —NH— or —NR$^a$— wherein R$^a$ is $C_1-C_6$ alkyl, and Alk is $C_1-C_6$ alkylene; and $R_5$ is hydrogen or a $C_1-C_6$ alkyl group;

$R_6$ is hydrogen, $C_1-C_6$ alkyl, phenyl($C_1-C_6$ alkyl) or heterocyclyl($C_1-C_6$ alkyl);

$R_7$ is is hydrogen or a $C_1-C_6$ alkyl group;

or (when $R_7$ is hydrogen) $R_3$ and $R_7$ taken together with the carbon atoms to which they are attached form a 2-hydroxycyclohexyl or $C_6$ sugar (hexose) ring;

or $R_6$ and $R_7$ taken together with the carbon atom to which they are attached form a 5 or 6-membered carbocyclic or heterocyclic ring;

and salts hydrates and solvates thereof.

As used herein the term "($C_1-C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, pentyl and hexyl.

The term "($C_2-C_6$)alkenyl" means a straight or branched chain alkenyl moiety having from 2 to 6 carbon atoms having at least one double bond of either E or Z stereochemistry where applicable. This term would include, for example, vinyl, allyl, 1-and 2-butenyl and 2-methyl-2-propenyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 4–8 carbon atoms and includes, for example, cyclohexenyl, cyclooctenyl, cycloheptenyl, cyclopentenyl, and cyclobutenyl. In the case of cycloalkenyl rings of from 5–8 carbon atoms, the ring may contain more than one double bond.

The unqualified term "heterocyclyl" or "heterocyclic" as used herein means a 5–7 membered aromatic or non-aromatic heterocyclic ring containing one or more heteroatoms selected from S, N and O, and optionally fused to a carbocyclic or second heterocyclic ring. Specific examples of such groups include pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, and benzimidazolyl. The term encompasses a 5- or 6-membered N-heterocyclic ring which (a) is attached via the N atom, (b) optionally contains N, O and/or S, SO or $SO_2$ as an additional ring member, (c) is substituted by oxo on one or both C atoms adjacent to the linking N atom and (d) is optionally benz-fused or optionally substituted on one or more other C atoms by $C_1-C_6$alkyl, or oxo and/or on any additional N atoms by $C_1-C_6$alkyl, phenyl or heteroaryl. Examples of the latter class of heterocyclic groups include maleimido, succinimido, phthalimido, 1,2-dimethyl-3,5-dioxo-1,2 ,4-triazolidin-4-yl, 3,4,4-trimethyl-2,5-dioxo-1- imidazolidinyl, 2-methyl-3,5-dioxo-1,2,4-oxadiazol-4-yl, 3-methyl-2,4,5-trioxo-1-imidazolinyl, 2,5-dioxo-3-phenyl-1-imidazolidinyl-2-oxo-1-pyrrolidinyl, 2,5-dioxo-1-pyrrolidinyl, 2,6-dioxopiperidinylnaphththalimido (i.e. 1,3-dihydro-1,3-dioxo-2H-benz[f]iso-indol-2-yl), 1,3-dihydro-1-oxo-2H-benz[f]isoindol-2-yl, 1,3-dihydro-1,3-dioxo-2H-pyrrolo[3,4-b]quinolin-2-yl, 2,3-dihydro-1,3-dioxo-1 H-benz[d,e]isoquinolin-2-yl group or saccharinyl (1,1,3-trioxo-benz [3,4-d]isothiazol-2-yl).

The term "heteroaryl" as used herein means an aromatic 5 or 6 membered monocyclic aromatic heterocyclic group. Specific examples of the latter include thienyl, furyl, pyrrolyl, imidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl and triazinyl.

An "optionally substituted phenyl or heteroaryl group" is a phenyl or heteroaryl group which is either unsubstituted or is substituted (i) with 1, 2, 3 or 4 substituents, each of which independently may be selected from $C_1$–$C_6$ alkyl, $C_2$–$C_6$ alkenyl, $C_1$–$C_6$ alkoxy($C_1$–$C_6$ alkoxy), trifluoromethyl, halo, cyano (—CN), —CH$_2$CN, —CO$_2$H, —CO$_2$R, —CONH$_2$, —CONHR, —CON(R)$_2$, —OH, —OR, oxo-, —SH, —SR, —NHCOR, and —NHCO$_2$R wherein R is $C_1$–$C_6$ alkyl or benzyl; or (ii) with 0, 1, or 2 substituents, each of which independently is selected from those listed under (i) above, and with a phenyl, phenoxy, phenylthio, heteroaryl, heteroaryloxy or heteroarylthio group which may be unsubstituted or substituted with 1, 2, 3 or 4 substituents, each of which independently is selected from those listed under (i) above.

In all contexts except in "optionally substituted phenyl or heteroaryl", the term "substituted" as applied to any moiety herein means substituted with up to four substituents, each of which independently may be ($C_1$–$C_6$)alkyl, ($C_2$–$C_6$) alkenyl, ($C_2$–$C_6$) alkynyl, ($C_1$–$C_6$)alkoxy, hydroxy, mercapto, ($C_1$–$C_6$)alkylthio, amino, halo (including fluoro, chloro, bromo and iodo), trifluoromethyl, nitro, CN, —COOH, —CONH$_2$, —COOR$^A$, —NHCOR$^A$, —NHCO$_2$R$^A$, —CONHR$^A$, or —CONR$^A$R$^B$ wherein R$^A$ and R$^B$ are each independently a ($C_1$–$C_6$)alkyl, benzyl, or heterocyclyl($C_1$–$C_6$)alkyl- group.

The term "side chain of a natural or non-natural alpha-amino acid" means the group R in a natural or non-natural amino acid of formula NH$_2$—CH(R)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, phenolic or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituent may optionally be protected.

Examples of side chains of non-natural alpha amino acids include those referred to below in the discussion of suitable $R_3$ groups for use in compounds of the present invention.

The term "protected" when used in relation to an amino, hydroxy, mercapto, or carboxy group means a derivative of such a group which is substantially non-functional. Such groups are widely known, for example from the art of peptide synthesis, and are discussed in the widely used handbook by T. W. Greene and P. G. M. Wuts, Protective Groups in Organic Synthesis, 2nd Edition, Wiley, N.Y., 1991. For example, carboxyl groups may be esterified (for example as a $C_1$–$C_6$ alkyl ester), amino groups may be converted to amides (for example as a NHCOC$_1$–C$_6$ alkyl amide) or carbamates (for example as an NHC(=O)OC$_1$–C$_6$ alkyl or NHC(=O)OCH$_2$Ph carbamate), hydroxyl groups may be converted to ethers (for example an OC$_1$–C$_6$ alkyl or a O(C$_1$–C$_6$ alkyl)phenyl ether) or esters (for example a OC(=O)C$_1$–C$_6$ alkyl ester) and thiol groups may be converted to thioethers (for example a tert-butyl or benzyl thioether) or thioesters (for example a SC(=O)C$_1$–C$_6$ alkyl thioester).

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are at least two chiral centres in the compounds according to the invention because of the presence of asymmetric carbon atoms. The presence of these asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof. At present, the preferred stereochemistry is in general as follows:

C atom carrying the groups X and $R_1$ —S,

C atom carrying the triple unsaturated group—R,

C atom carrying the groups $R_3$ and Y—S, but mixtures in which the above configurations predominate are also contemplated.

Ar represents an optionally substituted phenyl or heteroaryl group. Heteroaryl Ar groups may be bonded to the rest of the molecule (I) via a ring carbon atom in Ar or via a ring nitrogen atom in Ar. Suitable heteroaryl groups include thienyl, furyl, pyrrolyl, imidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl and triazinyl.

When the group Ar is substituted in accordance with the definition of Ar in formula (I), preferably only one substituent in present. In 6 membered Ar groups, such as phenyl and pyridyl, the substituent is preferably in the 4-position of the ring relative to the bond connecting Ar to the rest of molecule (I). In 5 membered Ar groups, such as thienyl and furanyl, the substituent is preferably in the 3- or 4-position of the ring relative to the bond connecting Ar to the rest of molecule (I).

A sole substituent in Ar may be any of those defined above in part (i) of the definition of "optionally substituted phenyl or heteroaryl". Preferred such substituents include $C_1$–$C_6$ alkyl eg methyl, ethyl, n-propyl, n-butyl, n-pentyl and n-hexyl; $C_1$–$C_6$ alkoxy($C_1$–$C_6$ alkoxy), 2-methoxyethoxy, phenoxy, phenylthio, trifluoromethyl, halo, cyano (—CN), —CH$_2$CN, —OH, or —OR, wherein R is $C_1$–$C_6$ alkyl or benzyl.

Another sole substituent in Ar may be any of those defined above in part (ii) of the definition of "optionally substituted phenyl or heteroaryl". Preferred such substituents include a phenyl, phenoxy, phenylthio, heteroaryl (eg 2-, 3- or 4-pyridyl), heteroaryloxy (eg 2-, 3- or 4-pyridyloxy) or heteroarylthio ((eg 2-, 3- or 4-pyridylthio) group which is either unsubstitued or substituted with one substituent selected from $C_1$–$C_6$ alkyl eg methyl, ethyl, n-propyl, n-butyl, n-pentyl and n-hexyl; $C_1$–$C_6$ alkoxy($C_1$–$C_6$ alkoxy), 2-methoxyethoxy, phenoxy, phenylthio, trifluoromethyl, halo, cyano (—CN), —CH$_2$CN, —OH, and —OR, wherein R is C$_1$–C$_6$ alkyl or benzyl.

Again the preferred location of a single substituent in a phenyl or heteroaryl-substituted Ar group is the 4-position of phenyl or 6 membered heteroaryl groups or the 3- or 4-position of 5 membered heteroaryl groups, relative to the bond connecting the phenyl or heteroaryl goup to Ar.

Examples of particular R$_1$ groups are hydrogen, C$_1$–C$_4$ alkyl, cyclopentyl, hydroxy, methoxy, allyl, or a group —(CH$_2$)$_t$—W wherein t represents 1, 2, 3 or 4 and W represents phthalimido, 1,2-dimethyl-3,5-dioxo-1,2,4-triazolidin-4-yl, 3,4,4-trimethyl-2,5-dioxo-imidazolidinyl, 2-methyl-3,5-dioxo-1,2,4-oxad iazol-4-yl, 3-methyl-2, 4,5-trioxo-1-imidazolidinyl, 2,5-dioxo-3-phenyl-1-imidazolidinyl-2-oxo-1-pyrrolidinyl, 2,5-dioxo-1-pyrrolidinyl, 2,6-dioxopiperidinylnaphththalimido (ie 1,3-dihydro-1,3-dioxo-2H-benz[f]isoindol-2-yl, 1,3-dihydro-1-oxo-2H-benz[f]isoindol-2-yl, 1,3-dihydro-1,3-dioxo-2H-pyrrolo[3,4-]quinolin-2-yl, 2,3-dihydro-1,3-dioxo-1H-benz[d,e]isoquinolin-2-yl or saccharinyl.

The following classes of substituent R$_3$ are suitable for use in compounds of the present invention:

(C$_1$–C$_6$)alkyl, benzyl, hydroxybenzyl, benzyloxybenzyl, (C$_1$–C$_6$)alkoxybenzyl, or benzyloxy(C$_1$–C$_6$)alkyl group; and the characterising group of a natural α-amino acid, in which any functional group may be protected, any amino group may be acylated and any carboxyl group present may be amidated; and a group -[Alk]$_n$R$_{22}$ where Alk is a (C$_1$–C$_6$)alkyl or (C$_2$–C$_6$)alkenyl group optionally interrupted by one or more —O—, or —S— atoms or —N(R$_{23}$)— groups [where R$_{23}$ is a hydrogen atom or a (C$_1$–C$_6$)alkyl group], n is 0 or 1, and R$_{22}$ is an optionally substituted cycloalkyl or cycloalkenyl group; and a benzyl group substituted in the phenyl ring by a group of formula —OCH$_2$COR$_{24}$ where R$_{24}$ is hydroxyl, amino, (C$_1$–C$_6$)alkoxy, phenyl(C$_1$–C$_6$)alkoxy, (C$_1$–C$_6$) alkylamino, di((C$_1$–C$_6$)alkyl)amino, phenyl(C$_1$–C$_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; and a heterocyclic((C$_1$–C$_6$)alkyl group, either being unsubstituted or mono- or di-substituted in the heterocyclic ring with halo, nitro, carboxy, (C$_1$–C$_6$)alkoxy, cyano, (C$_1$–C$_6$)alkanoyl, trifluoromethyl (C$_1$–C$_6$)alkyl, hydroxy, formyl, amino, (C$_1$–C$_6$) alkylamino, di-(C$_1$–C$_6$)alkylamino, mercapto, (C$_1$–C$_6$)alkylthio, hydroxy(C$_1$–C$_6$) alkyl, mercapto(C$_1$–C$_6$)alkyl or (C$_1$–C$_6$)alkylphenylmethyl;

a group —CR$_a$R$_b$R$_c$ in which:

each of R$_a$, R$_b$ and R$_c$ is independently hydrogen, (C$_1$–C$_6$)alkyl, (C$_2$–C$_6$) alkenyl, (C$_2$–C$_6$)alkynyl, phenyl(C$_1$–C$_6$)alkyl, (C$_3$–C$_8$)cycloalkyl, the foregoing being subject to the proviso that R$_a$, R$_b$ and R$_c$ are not all hydrogen; or R$_c$ is hydrogen, (C$_1$–C$_6$)alkyl, (C$_2$–C$_6$)alkenyl, (C$_2$–C$_6$) alkynyl, phenyl (C$_1$–C$_6$)alkyl, or (C$_3$–C$_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring (for example adamantyl); or R$_a$ and R$_b$ are each independently (C$_1$–C$_6$)alkyl, (C$_2$–C$_6$)alkenyl, (C$_2$–C$_6$) alkynyl, phenyl(C$_1$–C$_6$)alkyl, or a group as defined for R$_c$ below other than hydrogen, or R$_a$ and R$_b$ together with the carbon atom to which they are attached form a 3 to 8 membered cycloalkyl or a 3- to 8-membered heterocyclic ring, and R$_c$ is hydrogen, —OH, —SH, halogen, —CN, —CO$_2$H, (C$_1$–C$_4$)perfluoroalkyl, —CH$_2$OH, —CO$_2$(C$_1$–C$_6$)alkyl, —O(C$_1$–C$_6$) alkyl, —O(C$_2$–C$_6$) alkenyl, —S(C$_1$–C$_6$)alkyl, —SO (C$_1$–C$_6$)alkyl, —SO$_2$(C$_1$–C$_6$) alkyl, —S(C$_2$–C$_6$) alkenyl, —SO(C$_2$–C$_6$)alkenyl, —SO$_2$(C$_2$–C$_6$) alkenyl or a group —Q—W wherein Q represents a bond or —O—, —S—, —SO— or —SO$_2$— and W represents a phenyl, phenylalkyl, (C$_3$–C$_8$)cycloalkyl, (C$_3$–C$_8$)cycloalkylalkyl, (C$_4$–C$_8$) cycloalkenyl, (C$_4$–C$_8$)cycloalkenylalkyl, heteroaryl or heteroarylalkyl group, which group W may optionally be substituted by one or more substituents independently selected from, hydroxyl, halogen, —CN, —CO$_2$H, —CO$_2$(C$_1$–C$_6$)alkyl, —CONH$_2$, —CONH(C$_1$–C$_6$) alkyl, —CONH(C$_1$–C$_6$alkyl)$_2$, —CHO, —CH$_2$OH, (C$_1$–C$_4$)perfluoroalkyl, —O(C$_1$–C$_6$)alkyl, —S(C$_1$–C$_6$)alkyl, —SO (C$_1$–C$_6$) alkyl, —SO$_2$(C$_1$–C$_6$)alkyl, —NO$_2$, —NH$_2$, —NH(C$_1$–C$_6$)alkyl, —N ((C$_1$–C$_6$)alkyl)$_2$, —NHCOO (C$_1$–C$_6$)alkyl, (C$_1$–C$_6$)alkyl, (C$_2$–C$_6$)alkenyl, (C$_2$–C$_6$)alkynyl, (C$_3$–C$_8$) cycloalkyl, (C$_4$–C$_8$)cycloalkenyl, phenyl or benzyl.

Examples of particular R$_3$ groups suitable for inclusion in the compounds of the invention include methyl, benzyl, 4-chlorophenylmethyl, 2-thienylmethyl, iso-butyl or t-butyl, 1-benzylthio-1-methylethyl, and 1-mercapto-1-methylethyl or 3H-imidazol-4-ylmethyl. Presently preferred are compounds in which R$_3$ is benzyl, t-butyl 1-mercapto-1-methylethyl or 3H-imidazol-4-ylmethyl.

In compounds of the invention wherein Y is a group (ID), R$_4$ may for example be cyclopropyl, cyclobutyl, cyclopentyl, cyclohexyl cycloheptyl or cyclooctyl;

optionally substituted phenyl, napthyl, furanyl, thienyl, pyrrolinyl, tetrahydrofuranyl, imidazolyl, oxadiazolyl, thiazolyl, thiadiazolyl, pyridinyl, pyridinyl N-oxides, piperazinyl, indolyl, benzimidazolyl, benzotriazolyl, pyrazinyl, pyridazinyl, pyrimidinyl, dithianyl, benzo[b]thienyl, isoxazolyl or quinolinyl. Examples of particular R$_4$ groups of this type include phenyl, 2-methoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylphenyl, 4-t-butylphenyl, 4-t-butyl-2,6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl, 3-trifluoromethylphenyl, 4-trifluoromethylphenyl, 3,5-ditrifluoro-methylphenyl, 2-aminophenyl, 3-aminophenyl, 4-aminophenyl, 2-N,N-dimethyl-aminophenyl, 3-N,N-dimethylaminophenyl, 4-N,N-dimethylaminophenyl, 2-hydroxyphenyl, 3-hydroxyphenyl, 4-hydroxyphenyl, 2-napthyl, furan- 2-yl, thien-2-yl, pyrrol-2-yl, tetrahydrofuran-2-yl, imidazol-2-yl, thiazol-2-yl, 4-ethoxycarbonyl-methylthiazol-2-yl, 4-phenylthiazol-2-yl, 4,5-dimethylthiazol-2-yl, 5-bromothiazol-2-yl, 4-terf-butylthiazol-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, 5-methyl-,3,4-thiadiazol-2-yl, pyridin-2-yl, pyridin-3-yl, pyridin-4-yl, N-oxides of pyridin-2-yl pyridin-3-yl and pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl, quinolin-3-yl. Presently preferred are compounds in which $R_4$ is phenyl, 3-methoxyphenyl, pyridin-2-yl, pyridin-3-yl, and thiazol-2-yl, 4,5-dimethylthiazol-2-yl, 5-bromothiazol-2-yl, 4-ethoxycarbonyl methylthiazol-2-yl, 5-methyl-1,3,4-thiadiazol-2-yl or 4-tertbutylthiazol-2-yl. Particularly preferred $R_4$ groups of this type are 3-methoxyphenyl, pyridin-2-yl, pyridin-3-yl, pyridin-4-yl, thiazol-2-yl, 4-ethoxycarbonylmethylthiazol-2-yl, 5-methyl-1,3,4-thiadiazol-2-yl or 4-terf-butylthiazol-2-yl;

a group —CHR$^x$R$^y$ wherein R$^x$ and R$^y$ independently represent optionally substituted phenyl, thienyl, furyl, pyrrolyl, imidazolyl, thiazolyl, pyrazolyl, isoxazolyl, isothiazolyl, triazolyl, thiadiazolyl, oxadiazolyl, pyridinyl, pyridazinolyl, pyrimidinyl, piperazinyl or triazinyl. Examples of particular R$^x$ and R$^y$ include phenyl, 4-chlorophenyl and pyridinyl. Where R$^x$ and R$^y$ are linked covalently, an example of a group $R_4$ is 9-H-fluoren-9-yl;

a polyether chain possessing at least two non-adjacent oxygen atoms, for example 2-(2-methoxyethoxymethoxy)ethyl, 1,1-dimethyl-2-(2-methoxyethoxymethoxy) ethyl, 2-(2-ethoxyethoxymethoxy)ethyl, 2-(2-(2-methoxyethoxy)ethoxy)ethyl, 2-(2-(3-methoxypropoxymethoxy)ethyl, 3-(2-methoxyethoxymethoxy) propyl, 2,2-dimethyl-3-(2-methoxyethoxymethoxy)propyl, 2-(2-methoxyethoxy)ethyl, 3-(2-methoxyethoxy)-propyl, 2-methyl-2,2-di(2-methoxyethyl) propyl, 2-methyl-2,2-di(2-methoxyethyl)butyl, and 2-methyl-2,2-di(2-methoxymethyl)propyl. A presently preferred $R_4$ group of this type is 2-(2-methoxyethoxy) ethyl;

methyl, ethyl, n- or iso-propyl, n-, sec- or tert-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone)propyl, morpholin-4-ylpropyl, optionally substituted phenylethyl, phenylpropyl, phenylbutyl, or phenylpentyl. Presently preferred $R_4$ groups of this type are hydrogen, methyl or morpholin-4-ylpropyl.

In compounds of the invention wherein Y is a group (ID), where $R_3$ and $R_4$ taken together represent a divalent chain of formula —C(R$^a$)(R$^b$)—A—Alk— wherein R$^a$ and R$^b$ are independently hydrogen or $C_1$–$C_6$ alkyl, A is a bond, —O—, —S—, —S—S—, —NH— or —NR$^a$— wherein R$^a$ is $C_1$–$C_6$ alkyl, and Alk is $C_1$–$C_6$ alkylene, examples of such divalent chains include —C(CH$_3$)$_2$SCH$_2$CH$_2$CH$_2$—, and —C(CH$_3$)$_2$SSCH$_2$CH$_2$—.

In compounds of the invention wherein Y is a group (ID), examples of particular $R_5$ groups include hydrogen, methyl and ethyl. Presently preferred are compounds in which $R_5$ is methyl.

In compounds of the invention wherein Y is a group (IE), $R_6$ may be, for example, hydrogen, methyl, ethyl, benzyl or pyridylmethyl, and $R_7$ may be, for example hydrogen or methyl. $R_6$ and $R_7$ taken together with the carbon atom to which they are attached may form, for example, a cyclopentyl, cyclohexyl or morpholino ring. Presently preferred are compounds in which $R_6$ and $R_7$ are both hydrogen.

In compounds of the invention wherein Y is a group (IE), when $R_7$ is hydrogen, $R_3$ and $R_6$ taken together with the carbon atoms to which they are attached may form a 2-hydroxycyclohexyl or a glucose ring.

In a preferred subclass of the compounds of formula (I) of the invention

Ar is phenyl or 4-substituted phenyl, examples of the latter being 4-phenyl-phenyl, 4-phenoxy-phenyl, 4-(4'-chlorophenyl)-phenyl, 4-(4-cyanophenyl)-phenyl, 4-(4'-methoxy)-phenyl, 4-[4'-(2-methoxyethoxy) phenyl]-phenyl, 4-(pyridin-4-yl)-phenyl, 4-(pyridin-4-yloxy)-phenyl, 4-(4'-bromophenyl)-phenyl, 4-trifluoromethyl-phenyl, 4-fluorophenyl, 4-methoxyphenyl, 4-methoxyethoxyphenyl, 4-propylphenyl, 4-methylphenyl and 4-chlorophenyl;

m is 1 or 2;

n is 1;

X is —CONHOH, $R_1$ is hydrogen, $C_1$–$C_4$alkyl, cyclopentyl, hydroxy, methoxy, allyl, or a group—(CH$_2$)$_t$-W wherein t represents 1, 2, 3 or 4 and W represents phthalimido, 1,2-dimethyl-3,5-dioxo-1,2,4-triazolidin-4-yl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl-2-oxo-1-pyrrolidinyl, 2,5-dioxo-1-pyrrolidinyl or 2,6-dioxo-piperidinyinaphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b] quinolin-2-yl, 2,3-dihydro-1,3-dioxo-1H-benz[d,e]isoquinolin-2-yl or saccharinyl;

$R_3$ represents t-butyl or 1-benzylthio-1-methylethyl, benzyl, methyl, or 3H-imidazol-4-ylmethyl;

Y is a group of formula (ID) wherein $R_4$ represents cyclopropyl, cyclobutyl, cyclopentyl, cyclohexyl, cycloheptyl or cyclooctyl;

phenyl, 3-methoxyphenyl, pyridin-2-yl, pyridin-3-yl, thiazol-2-yl, 4-ethoxycarbonylmethylthiazol-2-yl, 5-methyl-1,3,4-thiadiazol-2-yl or 4-tert-butylthiazol-2-yl;

a group -CHR$^x$R$^y$ wherein R$^x$ and R$^y$ independently represent phenyl or 4-chlorophenyl or R$^x$ and R$^y$ are linked covalently in a 9-H-fluoren-9-yl ring;

a polyether chain possessing at least two non-adjacent oxygen atoms, for example 2-(2-methoxyethoxy) ethyl; or hydrogen, methyl or 3-morpholin-4-ylpropyl;

or $R_3$ and $R_4$ taken together represent —C(CH$_3$)$_2$SCH$_2$CH$_2$CH$_2$—, or —C(CH$_3$)$_2$SSCH$_2$CH$_2$—; and $R_5$ represents hydrogen or methyl;

or Y is a group of formula (IE) wherein $R_6$ and $R_7$ are both hydrogen;

and salts, hydrates and solvates thereof.

Interesting compounds of the invention include 3R-(3-biphenyl-4-yl-prop-2-ynyl)-N$^4$-(2,2-dimethyl-1S-methylcarbamoyl-propyl)-2S, N$^1$-dihydroxy-succinamide;

N$^4$-(2,2-dimethyl-1S-methylcarbamoyl-propyl)-2S,N$^1$-dihydroxy-3R-(3-phenyl-prop-2-ynyl)-succinamide;

N[4]-(2,2-dimethyl-1S-methylcarbamoyl-propyl )-2S, N[1]-dihydroxy-3R-(3-[4-trifluoromethyl-phenyl-prop-2-ynyl )-succinamide;

3R-[3-(4-chloro-phenyl)-prop-2-ynyl]-N[4]-(2,2-dimethyl-1S-methylcarbamoyl-propyl)-2S ,N[1]-dihydroxy-succinamide;

N[4]-(2,2-dimethyl-1S-methylcarbamoyl-propyl)-2S,N[1]-dihydroxy-3R-[3-(4-methoxy-phenyl)-prop-2-ynyl]-succinamide, 3R-[3-(4'-chloro-biphenyl-4-yl)-prop-2-ynyl]-N[4]-(2, 2-dimethyl-1 S-methylcarbamoyl-propyl)-2S,N[1]-dihydroxy-succinamide, 3R-[3-(4-cyanophenyl)-prop-2-ynyl]-N[4]-(2,2-dimethyl-1 S-methylcarbamoyl-propyl)-2S, N[4]-dihydroxy-succinamide, 3R-[3-(4-chloro-phenyl)-prop-2-ynyl]-N[4]-[2, 2-dimethyl-1 S-(3-morpholin-4-yl-propylcarbamoyl)-propyl]-2S ,N[1]-dihydroxy-succinamide, N[4]-(2,2-dimethyl-1 S-methylcarbamoyl-propyl)-2S, N[1]-dihydroxy-3-{3-[4-(2-methoxy-ethoxy)-phenyl]-prop-2-ynyl}-succinamide, 3R-[3-(4-chloro-phenyl )-prop-2-ynyl]-2S,N[1]-d ihydroxy-N[4]-{1 S-[2-(2-methoxy-ethoxy)-ethylcarbamoyl]-2,2-dimethyl-propyl}-succinamide, 3R-[3-(2-chloro-phenyl)-prop-2-ynyl]-N[4]-(2,2-dimethyl-1 S-methylcarbamoyl-propyl)-2S, N[1]-dihydroxy-succinamide, 3R-[3-(4-chloro-phenyl)-prop-2-ynyl]-N[4]-(1S-dimethylcarbamoyl-2,2-dimethyl-propyl)-2S, N[1]-dihydroxy-succinamide, N[4]-(2,2-dimethyl-1S-methylcarbamoyl-propyl )-2S,N[1]-dihyd roxy-3R-(5-phenyl-penta-2 ,4-diynyl)-succinamide, N[4]-(1S-benzyl-2-hydroxy-ethyl )-3R-[3-(4-Chloro-phenyl )-prop-2-ynyl]-2S,N[1]-dihydroxy-succinamide, 2,N[1]-dihydroxy-N[4]-(1-hydroxymethyl-3-methyl- butyl) -3 R-(5-phenyl-penta-2, 4,diynyl)-succinamide, and salts, hydrates and solvates thereof.

Further specific compounds of the invention are:

N[4]-(1S-d imethylcarbamoyl-2,2-dimethyl-propyl )-2S, N[1]-dihydroxy-3R-[3-(4-methoxy-phenyl)-prop-2-ynyl]-succinamide, 3R-(3-biphenyl-4-yl-prop-2-ynyl)-N[4]-(1S-dimethylcarbamoyl-2,2-dimethyl-propyl)-2S, N[1]-dihydroxy-succinamide, 3R-[3-(4'-chloro-biphenyl-4-yl)-prop-2-ynyl]-N[4]-(1S-dimethylcarbamoyl-2, 2-dimethyl-propyl)-2S,N[1]-dihydroxy-succinamide, 3R-[3-(4-chloro-phenyl)-prop-2-ynyl]-2S,N[1]-dihydroxy-N[4]-(1S-hydroxymethyl-2 ,2-dimethyl-propyl)-succinamide, 3R-[3-(4-chloro-phenyl)-prop-2-ynyl]-2S,N[1]-dihydroxy-N[4]-[2-hydroxy-1 -(3 H-imidazol-4-ylmethyl)-ethyl)-succinamide, 3R-[3-(4'-chloro-biphenyl-4-yl)-prop-2-ynyl]-2S, N[1]-dihydroxy-N[4]-(2-hydroxy-1S-methyl-ethyl)-succinamide, N[4]-(1S-benzyl-2-hydroxy-ethyl)-3R-(3-biphenyl-4-yl-prop-2-ynyl)-2S, N[1]-dihydroxy-succinamide, 3R-[3-(4-chloro-phenyl)-prop-2-ynyl]-N[4]-(1 S-dimethylcarbamoyl-2, 2-dimethyl-propyl)-N[1]-hydroxy-succinamide, N[4]-(2-benzylsulfanyl-1S-dimethylcarbamoyl-2-methyl-propyl)-3R-[3-(4-chloro-phenyl)-prop-2-ynyl]-2S,N[1]-dihydroxy-succinamide, 3R-[3-(4-chloro-phenyl )-prop-2-ynyl]-N[4]-(2, 2-dimethyl- 1S-methylcarbamoyl-propyl)-N[1]-hydroxy-2S-methoxy-succinamide and salts, hydrates and solvated thereof.

Compounds according to the present invention in which X is a hydroxamic acid group, —CONHOH may be prepared from corresponding compounds of the invention in which X is a carboxylic acid group —COOH or from the corresponding protected hydroxamic acid derivatives. That process, which forms another aspect of the invention, comprises causing an acid of general formula (II)

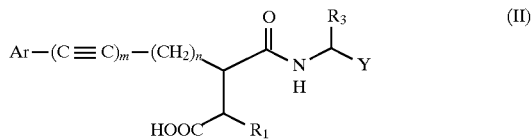

or an activated derivative thereof to react with hydroxylamine, O-protected hydroxylamine, or an N,O-diprotected hydroxylamine, or a salt thereof, Ar, m, n, $R_1$, $R_3$, and Y being as defined in general formula (I) except that any substituents in Ar, $R_1$, $R_3$, a nd Y which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in Ar, $R_1$, $R_3$, and Y. In particular, when Y is a group of formula (IE), the terminal hydroxy group may optionally be protected during the foregoing reaction.

Conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, O-tert-butyldimethylsilylhydroxylamine and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyldimethylsilylhydroxylamine, N-tert-butoxycarbonyl-O-tetrahydropyranylhydroxylamine, and N,O-bis(tert-butoxycarbonyl)hydroxylamine.

In the special case where $R_1$ in compound (I) is hydroxy, a particularly useful technique may be reaction of hydroxylamine with a dioxalone of formula (IIa):

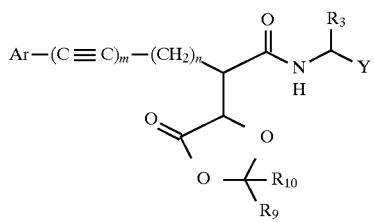

(IIa)

wherein the groups $R_9$ and $R_{10}$ are derived from a dioxalone forming reagent, and may be, for example, hydrogen, alkyl eg methyl, phenyl or substituted phenyl. The dioxalone ring is opened on reaction with hydroxylamine to give the required hydroxamic acid derivative of formula (I).

Compounds according to the present invention wherein X is a carboxylic acid group —COOH, ie compounds of formula (II) above, may be prepared by a process comprising: coupling an acid of formula (III) or an activated derivative thereof with an amine or aminoalcohol of formula (IV).

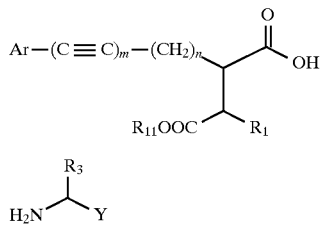

(III)

(IV)

wherein Ar, m, n, $R_1$, $R_3$, and Y being as defined in general formula (I) except that any substituents in Ar, $R_1$, $R_3$, and Y which are potentially reactive in the coupling reaction may themselves be protected from such reaction, and $R_{11}$ represents a hydroxy protecting group, and subsequently removing the protecting group $R_{11}$ and any protecting groups from Ar, $R_1$, $R_3$, and Y. In particular, when Y is a group of formula (IE), the terminal hydroxy group may optionally be protected during the coupling reaction of (IV) with (III).

An alternative procedure for the preparation of compounds of formulae (II)/(IIa) wherein Y is a group of formula (ID) and $R_5$ is H involves a Ugi 4-component condensation reaction between (III) and ammonia, an aldehyde ($R_3$CHO) and an isonitrile ($CNR_4$), as described in WO 96/26918.

Active derivatives of acids (III) include activated esters such as the pentafluorophenyl ester, acid anhydrides and acid halides, eg chlorides. Suitable hydroxy protecting groups may be selected from those known in the art.

Amino acid amides and amino alcohols of formula (IV) are either known or are prepared by routine known synthetic methods. Compounds of formula (III) may in many cases be prepared by alkylation of a compound of formula (V) with a halide of formula (VI)

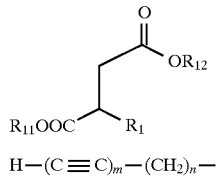

(V)

H—(C≡C)$_m$—(CH$_2$)$_n$—L  (VI)

wherein $R_1$, m and n are as defined in relation to formula (I) $R_{11}$ and $R_{12}$ are carboxyl protecting groups, and L is a reactive halo group (eg bromo) capable of reacting with (V) at the C atom adjacent the —COOR$_{12}$ group with elimination of the elements of HL and then reacting the resultant compound of formula (VII) with a halide of formula (VIII) under palladium catalysis (the Heck reaction; see R. F. Heck, *Palladium Reagents in Organic Synthesis*, Academic Press, London 1985).

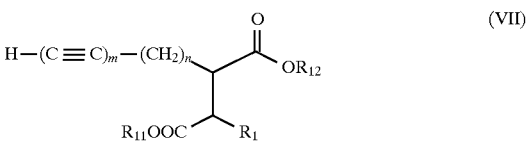

(VII)

Ar—L  (VIII)

again with elimination of the elements of HL, and thereafter removing protecting group $R_{12}$ or removing both protecting groups $R_{11}$ and $R_{12}$ and reprotecting the carboxylic acid group adjacent the group $R_1$. The terminal hydrogen of compound (VI) may optionally be protected during the reaction of (VI) with (V), for example as a silyl derivative such as trimethylsilyl. In the specific case where $R_1$ is hydroxy, the protected intermediate (VIIa) is suitable:

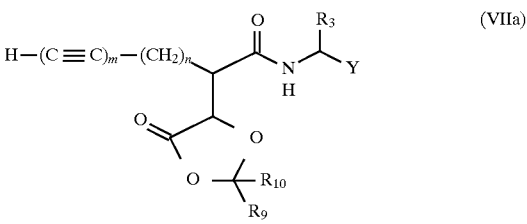

(VIIa)

wherein $R_9$ and $R_{10}$ are as defined in relation to formula (IIa) above.

Compounds (VII) wherein $R_1$ is hydrogen and m is 1 may be prepared by ozonolysis of a compound (VIIb)

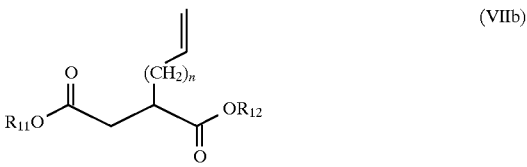

(VIIb)

wherein $R_{11}$ and $R_{12}$ are carboxyl protecting groups and n is as defined in formula (I), followed by treatment of the resulting compound (VIIc) with a compound (X) as generally described in Synlett, 1996, 521

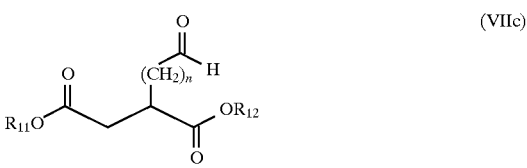

(VIIc)

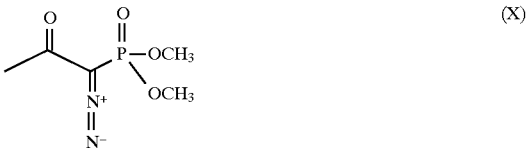

(X)

Compounds (VII) wherein $R_1$ is hydrogen and m is 2 may be prepared by reaction of a compounds (VII) wherein $R_1$ is hydrogen and m is 1 with a compound of formula (VIIIa)

Ar—C≡C—L  (VIIIa)

wherein L is a reactive halo group (eg bromo).

Yet another route to compounds (VII) where $R_1$ is hydrogen comprises alkylation of a compound (XI) with a compound (XII)

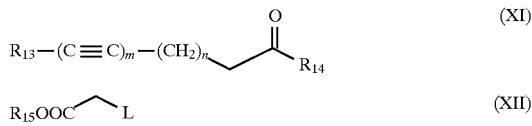

wherein $R_{13}$ is a protecting group such as trimethylsilyl, $R_{14}$ is a chiral auxiliary such as 4S-benzyloxyazolidin-2-one, $R_{15}$ is a carboxyl protecting group, and L is a leaving group such as a halide, to form (XIII)

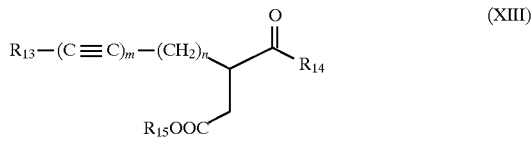

which is then deprotected and reprotected as appropriate to form the desired compound (VII).

Compounds (VII) wherein $R_1$ is hydrogen may be used as intermediates in the preparation of compounds wherein $R_1$ is one of a variety of substituents by known methods, eg alkylation (WO 94/21625), Claisen rearrangement (GB patent application No 9610985.5) or carboxylation followed by the Mannich and Michael reactions (WO 90/05719).

In some cases it may be possible to prepare compounds (III) using only one alkylation step, by reacting compound (V) with a compound of formula (IX)

wherein L is a reactive halo group (eg bromo) capable of reacting with (V) at the C atom adjacent the —COOR$_{12}$ group with elimination of the elements of HL.

As mentioned above, compounds of formula (I) are useful in human or veterinary medicine since they are active as inhibitors of MMPs.

Accordingly in another aspect, this invention concerns:
(i) a method of management (by which is meant treatment or prophylaxis) of diseases or conditions mediated by MMPs in mammals, in particular in humans, which method comprises administering to the mammal an effective amount of a compound as defined with respect to formula (I) above, or a pharmaceutically acceptable salt thereof; and
(ii) a compound as defined with respect to formula (I) for use in human or veterinary medicine, particularly in the management (by which is meant treatment or prophylaxis) of diseases or conditions mediated by MMPs; and
(iii) the use of a compound as defined with respect to formula (I) in the preparation of an agent for the management (by which is meant treatment or prophylaxis) of diseases or conditions mediated by MMPs.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases as well as neuroinflammatory disorders, including those involving myelin degradation, for example multiple sclerosis.

In a further aspect of the invention there is provided a pharmaceutical or veterinary composition comprising a compound of formula (I) together with a pharmaceutically or veterinarily acceptable excipient or carrier. One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 5 to 100 mg of a compound of the invention. A suitable daily dose for a mammal may vary widely depending on the condition of the patient. However, a dose of a compound of general formula I of about 0.1 to 10 mg/kg body weight, particularly from about .1 to 3 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint.

The examples which follow serve to illustrate the preparation of compounds the invention but are not intended to limit the scope in any way. Amino acid derivatives and amino alcohols were available commercially or were prepared according to literature methods. Unless stated otherwise, starting aryl and alkynyl halides were obtained from commercial suppliers.

The following abbreviations have been used throughout:
EDC N-Ethyl-N'(3-dimethylaminopropyl)carbodiimide hydrochloride
HOBt 1-Hydroxybenzotriazole
LDA Lithium diisopropylamide
THF Tetrahydrofuran
HPLC High Performance Liquid Chromatography $^1$H and $^{13}$C NMR spectra were recorded using a Bruker AC 250E spectrometer at 250.1 and 62.9 MHz, respectively. Elemental microanalyses were performed by MEDAC Ltd, Department of Chemistry, Brunel University, Uxbridge, Middlesex, UB8 3PH.

EXAMPLE 1

3R-(3-Biphenyl-4-yl-prop-2-ynyl)-$N^4$-(2,2-Dimethyl-1 S-methylcarbamoyl-propyl)-2S, $N^1$-dihydroxy-succinamide

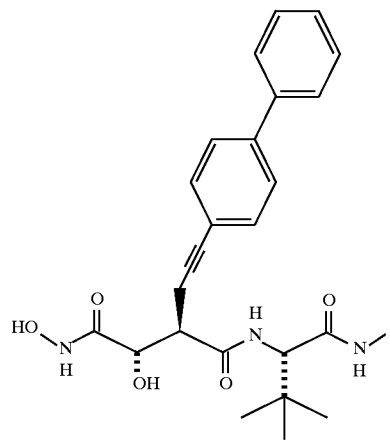

The title compound was prepared according to the route outlined in Scheme 1 and is described in detail below.

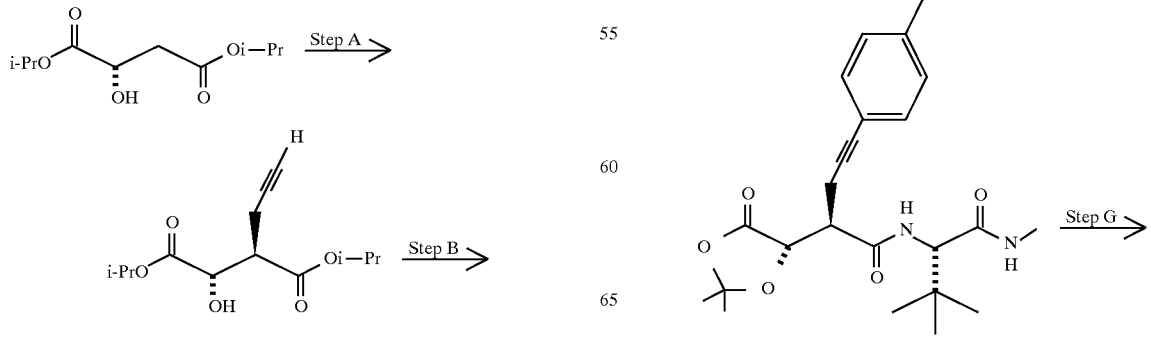

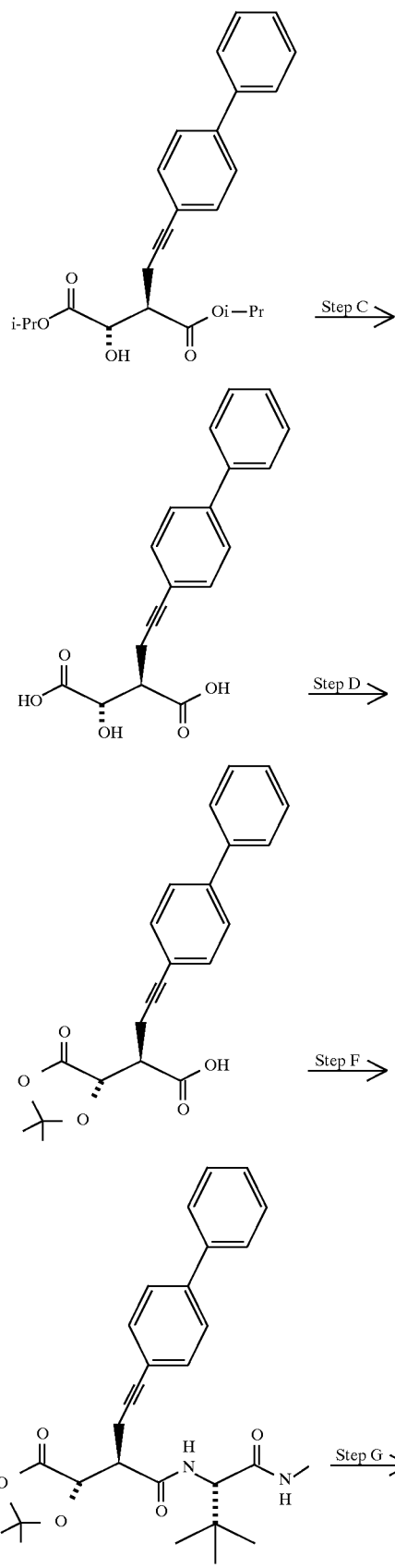

-continued
Scheme 1

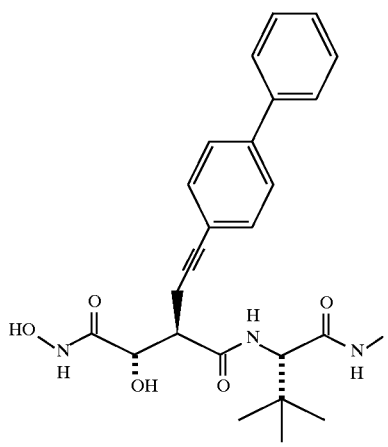

STEP A

2S-Hydroxy-3R-prop-2-ynyl-succinic acid diisopropyl ester

A solution of S-malic acid diisopropyl ester (5.5 g, 25.23 mmol) in dry THF (20 ml) was added to a solution of freshly prepared LDA [from N,N-diisopropylamine (6.9 ml, 52.5 mmol) and 2.5 M n-butyllithium (21 ml, 52.5 mmol)] in dry THF (50 ml), whilst maintaining the temperature at −5° C. The reaction mixture was stirred at −5° C. for 75 minutes then cooled to −70° C. A solution of propargyl bromide (80% solution in toluene, 3.10 ml, 27.75 mmol) was added slowly, whilst maintaining the temperature at −70° C. The cooling bath was removed and the solution was stirred overnight before quenching with saturated aqueous ammonium chloride (50 ml). The aqueous layer was separated and extracted with ethyl acetate (2×20 ml). The organic layers were combined and washed with 1M hydrochloric acid (2×20 ml) and brine (20 ml) and dried over anhydrous magnesium sulphate. The solution was filtered and concentrated in vacuo to give a brown oil which was purified by column chromatography (silica gel, 25% ethyl acetate in hexanes) to provide the title compound as an orange oil (1.4 g, 5.46 mmol, 22%; 9:1 mixture of diastereomers by NMR). $^1$H-NMR; δ (CDCl$_3$, major diastereoisomer), 5.12 (1H, m), 5.04 (1H, m), 4.45 (1H, dd, J=5.8, 2.6 Hz), 3.17 (1H, d, J=5.8 Hz), 3.08 (1H, ddd, J=5.8, 2.5 Hz), 2.67 (1H, m), 2.05 (1H, t, J=2.9 Hz), 1.29 (6H, d, J=6.1 Hz) and 1.19 (6H, d, J=6.2 Hz).

STEP B

3R-(3-Biphenyl-4-yl-prop-2-ynyl)-2S-hydroxy-succinic acid diisopropyl ester 2S-Hydroxy-3R-prop-2-ynyl-succinic acid diisopropyl ester (0.51 g, 2 mmol) and 4-bromobiphenyl (0.35 g, 1.5 mmol) were dissolved in diisopropylamine (4 ml) in a 5 ml Wheaton vial. Palladium (48 mg, 4.6 mol %) and copper (I) iodide (12 mg, 4.0 mol %) were added and the vial was sealed and heated at 130° C. for 3.5 hours then stirred at room temperature overnight. The solution was filtered through celite, flushing with dichloromethane (30 ml). The filtrate was washed with 1 M hydrochloric acid (2×20 ml) and brine (20 ml), dried (anhydrous magnesium sulphate) and filtered. The solvents were removed in vacuo and the residue was purified by column chromatography (silica gel, 25% ethyl acetate in hexanes) to provide the title compound as a yellow oil (0.42 g, 1.03 mmol, 68%). $^1$H-NMR; δ(CDCl$_3$), 7.53 (9H, m), 5.16 (1H, m), 5.06 (1H, m), 4.55 (1H, d, J=2.5 Hz), 3.2 (1H, ddd, J=5.5,2.5 Hz), 2.94 (2H, m), 1.32 (6H, d, J =6.3 Hz) and 1.25 (6H, d, J=6.2 Hz).

STEP C

3R-(3-Biphenyl-4-yl-prop-2-ynyl)-2S-hydroxy-succinic acid

A solution of 3R-(3-biphenyl-4-yl-prop-2-ynyl)-2S-hydroxy-succinic acid diisopropyl ester (0.7 g, 1.71 mmol) in 1M sodium hydroxide (6 ml, 6 mmol) was heated at reflux for 1 hour then cooled to room temperature. The solution was washed with dichloromethane (20 ml), acidified to pH 2 with 1M hydrochloric acid and extracted with ethyl acetate (3×10 ml). Organic extracts were combined, dried over anhydrous magnesium sulphate, filtered and evaporated to provide product as a light brown foam (0.48 g, 1.48 mmol, 86%). $^1$H-NMR; δ (CDCl$_3$), 7.55 (9H, m), 4.76 (1H, d, J=2.5 Hz), 4.18 (3H, br s), 3.37 (1H, m) and 3.01 (2H, m).

STEP D

5-Biphenyl-4-yl-2R-(2,2-dimethyl-5-oxo-[1,3]dioxolan-4S-yl)-pent-4-ynoic acid A solution of 3R-(3-biphenyl-4-yl-prop-2-ynyl)-2S-hydroxy-succinic acid (0.48 g, 1.48 mmol) in ethyl acetate (5 ml) and 2,2-dimethoxypropane (5 ml) containing a catalytic amount of p-toluenesulfonic acid (10 mg) was heated at reflux for 2.5 hours. Solvents were removed in vacuo to provide the title compound as a brown foam (0.55 g, 1.5 mmol, quantitative). $^1$H-NMR; δ (CDCl$_3$), 7.54 (9H, m), 4.88 (1H, d, J=2.5Hz), 3.33 (1H, m), 3.11 (1H, dd, J=17.2, 5.2 Hz), 2.92 (1H, dd, J=14.5, 4.4 Hz), 1.62 (3H, s) and 1.60 (3H, s).

STEP E

5-Biphenyl-4-yl-2R-(2,2-dimethyl-5-oxo-[1,3]dioxolan-4S-yl)-pent-4-ynoic acid (2,2-dimethyl-1 S-methylcarbamoyl-propyl)-amide To a solution of 5-biphenyl-4-yl-2R-(2,2-dimethyl-5-oxo-[1 ,3]dioxolan-4S-yl)-pent-4-ynoic acid (0.55 g, 1.5 mmol) in dichloromethane (20 ml) was added HOBt (0.22 g, 1.65 mmol) followed by EDC (0.36 g, 1.87 mmol). The mixture was heated at reflux for 1 hour then cooled to room temperature. L-tert-Leucine-N-methylamide (0.22 g, 1.5 mmol) was added and the resulting solution was heated at reflux for 4 hours. The solution was allowed to cool to room temperature and washed with 1M hydrochloric acid (20 ml), saturated sodium hydrogen carbonate (20 ml) and brine (20 ml), dried (magnesium sulphate), filtered and concentrated in vacuo. The product was purified by column chromatography (silica gel, 50% ethyl acetate in hexanes) to provide the title compound as a yellow solid (140 mg, 0.28 mmol, 19%). $^1$H-NMR; δ(CDCl$_3$), 7.54 (9H, m), 6.85 (1H, d, J=9.2 Hz), 6.45 (1H, m), 4.75 (1H, d, J=5.2 Hz), 4.34 (1H, d, j=9.2 Hz), 3.02 (3H, m), 2.73 (3H, d, J=4.8 Hz), 1.63 (3H, s), 1.57 (3H, s) and 1.02 (9H, s).

STEP F

3R-(3-Biphenyl-4-yl-prop-2-ynyl)-N$^4$-(2,2-Dimethyl- 1S-methylcarbamoyl-propyl)-N$^1$, 2S-dihydroxy-succinamide A suspension of sodium methoxide (46 mg, 0.85 mmol) and hydroxylamine hydrochloride (59 mg, 0.85 mmol) in methanol (2 ml) was stirred at room temperature for 1.5 hours then filtered into a solution of 5-biphenyl-4-yl-2R-(2, 2-dimethyl-5-oxo-[1,3]dioxolan-4S-yl)-pent-4-ynoic acid (2,2-dimethyl-1 S-methylcarbamoyl-propyl)-amide (140 mg, 0.28 mmol) and the resulting solution was stirred at room temperature overnight. Solvents were removed in vacuo and the residue was purified by column chromatography (acid-washed silica gel, 10% methanol in dichloromethane) to provide the title compound as a white solid (25 mg, 0.054 mmol, 19%). $^1$H-NMR; δ (CD$_3$OD), 7.97 (1H, s), 7.85 (1H, d, J=9.1 Hz), 7.32 (9H, m), 4.75 (1H, s), 4.17 (1H, dd, j=9.1, 3.5 Hz), 3.01 (1H, m), 2.66 (2H, m), 2.50 (3H, s), 1.74 (1H, d, J=2.8 Hz) and 0.09 (9H, s). $^{13}$C-NMR; δ (CD$_3$OD), 176.2, 175.4, 166.8, 144.4, 144.0, 135.6, 132.3, 131.1, 130.2, 126.1, 90.1, 85.8, 74.8, 64.7, 52.8, 38.0, 29.6, 28.4 and 23.0.

EXAMPLE 2

N$^4$-(2,2-Dimethyl-1S-methylcarbamoyl-propyl)-2S, N$^1$-dihydroxy-3R-(3-phenyl-prop-2-ynyl)-succinamide

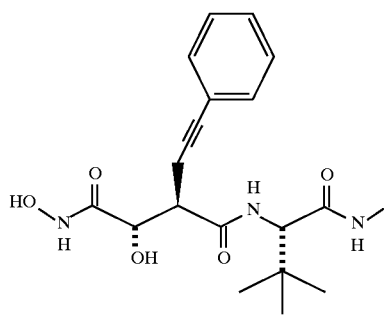

The title compound was prepared according to the route outlined in Scheme 2 and is described in detail below.

Scheme 2

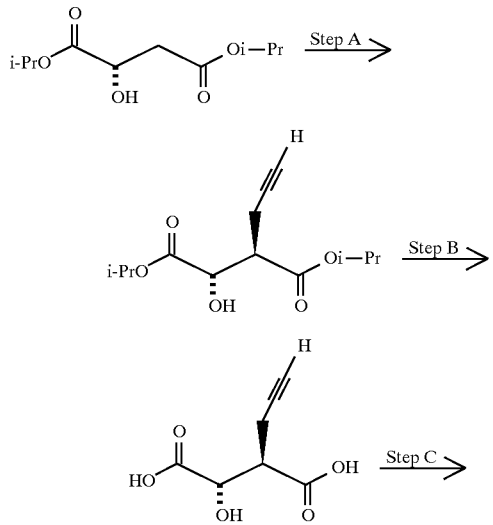

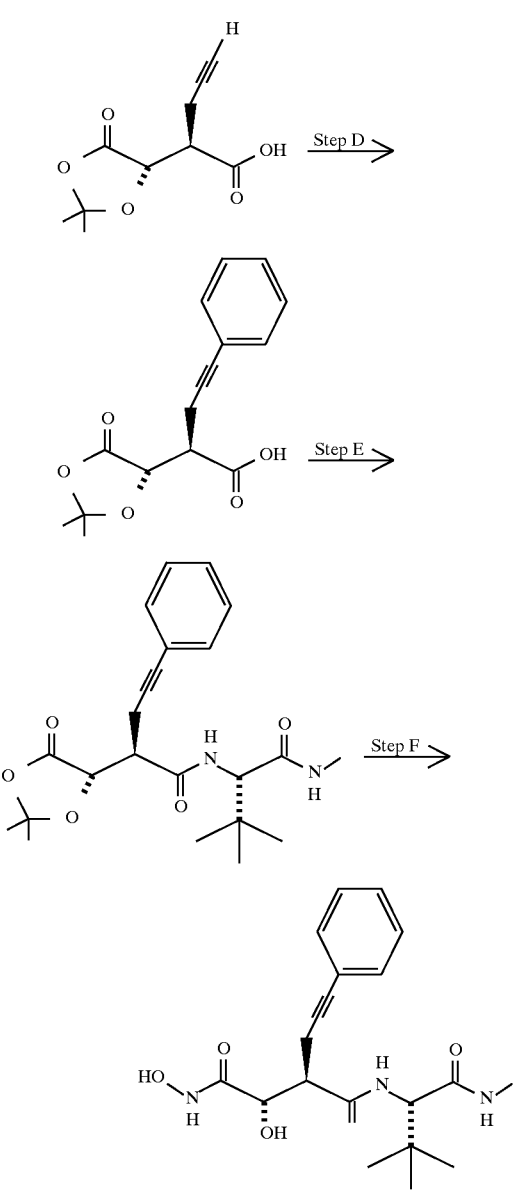

STEP A
Identical to example 1, step A

STEP B

2S-Hydroxy-3R-prop-2-ynyl-succinic acid

A solution of 2S-hydroxy-3R-prop-2-ynyl-succinic acid diisopropyl ester (2.47 g, 9.56 mmol) in 1M sodium hydroxide (32 ml, 32 mmol) was heated at reflux for 1 hour then cooled to room temperature. The solution was acidified to pH 2 with 1M hydrochloric acid and extracted with ethyl acetate (5×10 ml). The combined organics were dried over magnesium sulphate, filtered and concentrated in vacuo to provide the title compound as a brown oil (0.94 g, 6.18 mmol, 64%). $^1$H-NMR; δ (CD$_3$OD), 4.37 (1H, d, J =3.4 Hz), 3.01 (1H, m), 2.51 ( 2H, m), 2.21 (1H, t, J=2.5 Hz)

STEP C 2R-(2,2-Dimethyl-5-oxo-[1,3]dioxolan-4S-yl)-pent-4-ynoic acid

2S-Hydroxy-3R-prop-2-ynyl-succinic acid (0.94 g, 6.18 mmol) was dissolved in ethyl acetate (5 ml). Dimethoxypropane (10 ml) and p-toluenesulfonic acid (10 mg) were added and the solution heated at reflux for 2.5 hours. Solvents were removed in vacuo to provide the title compound as a dark brown gum (1.0 g, 5.2 mmol, 84%). $^1$H-NMR; δ (CDCl$_3$), 4.80 (1H, d, J=2.4 Hz), 3.22 (1H, m), 2.86 (1H, ddd, J=17.2, 5.4, 2.6 Hz) ,2.61 (1H, ddd, J=13.0, 10.3, 2.6 Hz), 2.10 (1H, t, J=2.8 Hz), 1.58 (3H, s) and 1,57 (3H, s).

STEP D 2R-(2,2-Dimethyl-5-oxo-[1,3]dioxolan-4S-yl)-5-phenyl-pent-4-ynoic acid 2R-(2,2-Dimethyl-5-oxo-[1,3]dioxolan-4S-yl)-pent-4-ynoic acid (3 g, 15.62 mmol) and iodobenzene (1.31 ml, 11.74 mmol) were dissolved in diisopropylamine (30 ml) in a 35 ml pressure tube. Dichlorobis(triphenylphosphine) palladium(II) (379 mg, 4.6 mo %) and copper (I) iodide (89 mg, 4.0 mo%) were added and the tube heated at 130° C. for 3.5 hours. The solution was filtered through celite, washing with dichloromethane (100 ml) and the organic solution washed with 1M hydrochloric acid (3×50 ml) then extracted with saturated aqueous sodium hydrogen carbonate (4×30 ml). The basic extracts were combined, acidified to pH2 with 1M hydrochloric acid then extracted with dichloromethane (3×30 ml). Combined organics were dried (magnesium sulphate), filtered and solvents removed in vacuo to provide the title compound as an orange solid (2.1 g, 7.83 mmol, 67%). 1H-NMR; δ(CDCl$_3$), 7.32 (5H, m), 4.86 (1H, d, J=3.0 Hz), 3.32 (1H, m), 3.10 (1H, dd, J=17.13, 5.2Hz), 2.88 (1H, dd, J=17.3, 10.4 Hz), 1.6 (3H, s) and 1.59 (3H, s).

STEP E 2R-(2,2-Dimethyl-5-oxo-[1,3]dioxalan-4S-yl)-5-phenyl-pent-4-ynoic acid (2, 2-dimethyl-1 S-methylcarbamoyl-propyl)-amide A solution of 2R-(2,2-dimethyl-5-oxo-[1,3]dioxolan-4S-yl)-5-phenyl-pent-4-ynoic acid (0.7 g, 2.61 mmol) and HOBt (0.42 g, 3.13 mmol) in dichloromethane (35 ml) was cooled to 0° C. and treated with EDC (0.63 g, 3.26 mmol). The ice bath was removed and the solution stirred for 2 hours. L-teit-Leucine-N-methyl amide (0.45 g, 3.13.mmol) was then added and the resulting solution was stirred at room temperature overnight. The solution was washed with 1M hydrochloric acid (2×20 ml), saturated aqueous sodium hydrogen carbonate (2×20 ml) and brine (20 ml), dried over anhydrous magnesium sulphate, filtered and concentrated in vacuo. The product was purified by column chromatography (silica gel, 50% ethyl acetate in hexanes) to provide the title compound as a yellow foam (0.25 g, 0.63 mmol, 24%). $^1$H-NMR; δ (CDCl$_3$), 7.29 (5H, m), 6.73 (1H, d, J=9.0 Hz), 6.06 (1H, m), 4.74 (1H, d, J=5.3 Hz), 4.23 (1H, d, j=9.2 Hz), 3.01 (2H, m), 2.87 (1H, dd, J=18.1 10.0 Hz), 2.71 (3H, d, J=4.8 Hz), 1.62 (3H, s), 1.57 (3H, s) and 1.00 (9H, s).

STEP F

N$^1$-(2,2-Dimethyl-1 S-methylcarbamoyl-propyl)-N$^4$-hydroxy-2R-(phenyl-4-yi-prop-2-ynyl)-3S-hydroxy-succinamide A suspension of sodium methoxide (102 mg, 1.9 mmol) and hydroxylamine hydrochloride (131 mg, 1.9 mmol) in methanol (5 ml) was stirred at room temperature for 1.5 hours then filtered into a solution of 2R-(2,2-dimethyl-5-oxo-[1, 3]dioxalan-4S-yl)-5-phenyl-pent-4-ynoic acid (2,2-dimethyl-1S-methylcarbamoyl-propyl)-amide (250 mg, 0.63 mmol) and the resulting solution was stirred at room temperature overnight. Solvents were removed in vacuo and the residue was purified by column chromatography (acid-washed silica gel, 10% methanol in dichloromethane) to provide the title compound as an off-white solid (77 mg, 31%). m.p. 186.5° 187° C. $^1$H-NMR; δ (CD$_3$OD), 7.23 (5H, m), 4.19 (1H, d, J=5.8 Hz), 4.15 (1H, s), 2.98 (1H, m), 2.63 (2H, dd, J=7.8Hz), 2.48 (3H, s) and 0.88 (9H, s). $^{13}$C-NMR; δ (CD$_3$OD), 176.2, 175.4, 135.1, 131.7, 131.4, 127.2, 89.4, 85.9, 64.7, 52.8, 38.0, 29.6, 28.4 and 22.9.

The following additional compounds were prepared by the method of Example 2, substituting the appropriate aryl/biaryl halide or 1-bromo-2-phenylacetylene for iodobenzene in Step D.

EXAMPLE 3

N$^4$-(2,2-Dimethyl- 1S-methylcarbamoyl-propyl )-2S, N$^1$-dihydroxy-3R-(3-[4-trifluoromethyl-phenyi-prop-2-ynyl)-succinamide

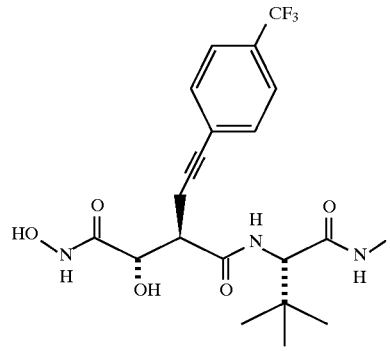

Pink solid. m.p. 186.5°–188° C. 1H-NMR; δ (CD$_3$OD), 7.47 (4H, m), 4.17 (2H, m), 3.00, (1H, m), 2.66 (2H, m), 2.48 (3H, s) and 0.88 (9H, s). $^{13}$C-NMR; δ(CD$_3$OD), 176.0, 175.4, 174.1, 135.6, 133.0 (d, J$_{CF}$=3.4 Hz), 127.9 (d, J$_{CF}$= 270.9 Hz), 92.7, 84.6, 74.6, 69.3, 64.2, 52.6, 38.0, 29.6, 28.3, 22.9 and 17.8. IR: v$_{max}$ (KBr), 3317, 2964, 2358, 1635, 1528, 1327, 1168, 1120, 1068 and 840 cm$^{-1}$.

EXAMPLE 4

3R-[3-(4-Chloro-phenyl)-prop-2-ynyl]-N$^4$-(2,2-dimethyl-1S-methylcarbamoyl-propyl)-2S, ,N$^1$-dihydroxy-succinamide

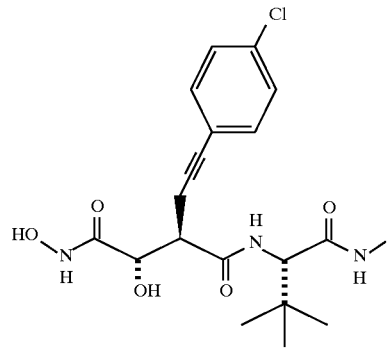

White solid. m.p. 215.5°–216° C. $^1$H-NMR; δ (CD$_3$OD), 7.21 (4H, m), 4.16 (2H, m), 2.96 (1H, m), 2.62 (2H, m), 2.50 (3H, s) and 0.88 (9H, s). $^{13}$C-NMR; δ(CD$_3$OD), 174.0, 173.4, 171.5, 135.2, 134.5, 129.9, 123.8, 88.7, 82.7, 72.5, 62.6, 50.6, 35.9, 27.5, 26.3 and 20.9. IR: V$_{max}$ (KBr), 3243, 2963, 2902, 2340, 1634, 1572, 1526, 1491, 1371, 1319, 1227, 1117, 1090 and 830 cm$^{-1}$.

EXAMPLE 5

N⁴-(2,2-Dimethyl-1S-methylcarbamoyl-propyl)-2S,N¹-dihydroxy-3R-[3-(4-methoxy-phenyl)-prop-2-ynyl]-succinamide

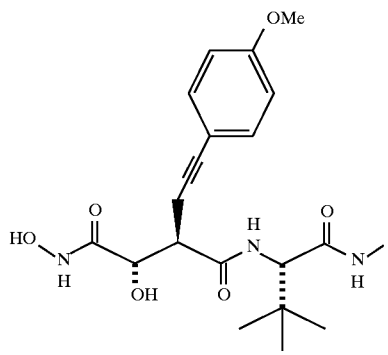

White solid. ¹H-NMR; δ((CD₃)₂SO), 8.87 (1H, s), 7.89 (1H, m), 7.65 (1H, d, J=9.5 Hz), 7.25 (2H, d, J=8.7 Hz), 6.87 (2H, d, J=8.7 Hz), 5.54 (1H, d, J=7.6 Hz), 4.24 (1H, d, J =9.5 Hz), 3.91 (1H, t, J=7.7 Hz), 3.74 (3H, s), 2.93 (1H, m), 2.57 (1H, m), 2.50 (3H, d, J=4.0 Hz), 2.38 (1H, dd, J=5.4, 16.5Hz) and 0.90 (9H, s). ¹³C-NMR; δ ((CD₃)₂ ₛₒ), 170.8, 170.3, 168.4, 136.0, 131.4, 115.2, 112.6, 185.9, 81.3, 71.7, 58.6, 56.3,54.0, 34.4, 27.7, 26.3 and 25.6.

EXAMPLE 6

3 R-[3-(4'-Chloro-biphenyl-4-yl)-prop-2-ynyl]-N⁴(2,2-dimethyl-1S-methylcarbamoy-propyl)-2S,N¹-dihydroxy-succinamide

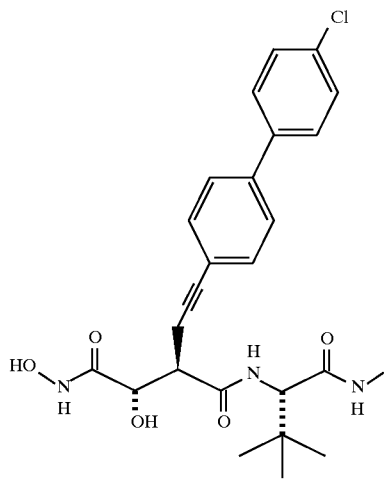

White solid. ¹H-NMR; δ ((CD₃)₂SO), 10.69 (1H, s), 8.89 (1H, s), 7.93 (1H, m), 7.70(2H, d, J=8.5 Hz), 7.64 (2H, d, J=8.1 Hz), 7.51 (2H, d, J=8.5 Hz), 7.42 (2H, d, =8.1 Hz), 5.58 (1H, d, J=7.6 Hz), 4.25 (1H, d, J=9.4 Hz), 3.93 (1H, d, J=7.6 Hz), 2.99 (1H, m), 2.51 (5H, m) and 0.90 (9H, s). ¹³C-NMR; δ ((CD₃)₂SO), 175.8, 175.5, 173.5, 143.1, 137.7, 137.1, 134.0, 133.4, 131.6, 127.6, 127.5, 94.0, 86.3, 75.6, 64.9, 53.6, 39.5, 31.8,30.3 and 24.1.

The starting material was prepared as follows:

A mixture of 4-chloro-iodobenzene (0.99 g, 4.15 mmol), (4-bromophenyl)boronic acid (1.0 g, 4.98 mmol), anhydrous potassium carbonate (860 mg, 6.22 mmol) and dichlorobis (triphenylphosphine) palladium (II) (87 mg, 0.12 mmol) in toluene (40 ml) was heated at 90° C. for 4 hours under an argon atmosphere. The solvent was removed under reduced pressure and the residue was dissolved in dichloromethane (50 ml). The organic solution was washed successively with 1M hydrochloric acid (2×30 ml), saturated aq. sodium hydrogen carbonate (2×30 ml) and brine, dried over anhydrous magnesium sulfate and filtered. The solvent was removed under reduced pressure to leave an orange solid, which was purifed by trituration with ethyl acetate-hexane (1:6) to provide 4'-chloro-4-bromo-biphenyl (0.5 g, 45%) as a pale orange solid. ¹H-NMR; δ (CDCl₃) 7.49 (m).

EXAMPLE 7

3R-[3-(4-Cyanophenyl)-prop-2-ynyl]-N⁴-(2,2-dimethyl-1S-methylcarbamoyl-propyl)-2S,N¹-dihydroxy-succinamide

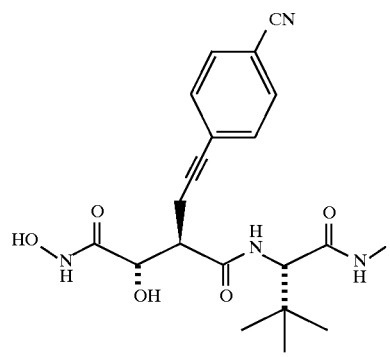

White solid. ¹H-NMR; δ (CD₃)₂SO), 10.68 (1H, s), 8.88 (1H, s), 7.91 (1H, d, J=4.3 Hz), 7.81 (2H, d, J=8.2 Hz), 7.73 (1H, d, J=9.5 Hz), 7.50 (2H, d, J=8.2 Hz), 5.56 (1H, br s), 4.24 (1H, d, J=9.5 Hz), 3.91 (1H, d, J=8.3 Hz), 2.58 (1H, dd, j=9.7, 16.8 Hz), 2.49 (4H, m) and 0.89 (9H, s). ¹³C-NMR; δ ((CD₃)₂SO), 175.7, 175.5, 173.4, 137.3, 133.1, 132.2, 123.6, 115.4, 97.7, 85.4, 75.6, 64.9, 53.3, 39.4, 31.7,30.2 and 24.1.

EXAMPLE 8

3R-[3-(4-Chloro-phenyl)-prop-2-ynyl]-N⁴[2,2-dimethyl-1S-(3-morpholin-4-yl-propylcarbamoyl)-propyl]-2S,N¹-dihydroxy-succinamide

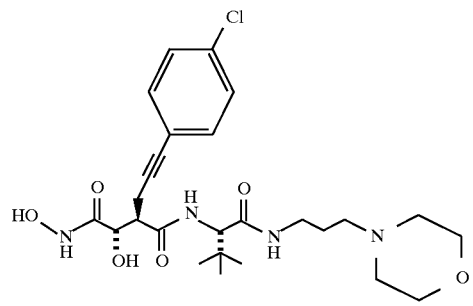

White solid. m.p. 108°–110° C. ¹H-NMR; δ (CD₃OD), 7.24 (4H, m), 4.30 (1H, d j =4.4 Hz), 3.98 (1H, s), 3.80 (4H, m), 3.12 (9H, m), 2.70 (2H, d, J=7.2 Hz), 1.85 (2H, m) and 0.92 (9H, s). ¹³C-NMR; δ (CD₃OD), 173.9, 173.5, 171.3, 135.0, 134.2, 129.6, 123.4, 88.5, 82.5, 71.5, 65.3, 63.2, 56.0, 53.3, 50.3, 36.9, 34.7, 27.2, 24.8 and 20.7.

EXAMPLE 9

N⁴-(2,2-Dimethyl-1S-methylcarbamoyl-propyl)-2S, N¹dihydroxy-3-{3-[4-(2-methoxy-ethoxy)-phenyl]-prop-2-ynyl}-succinamide

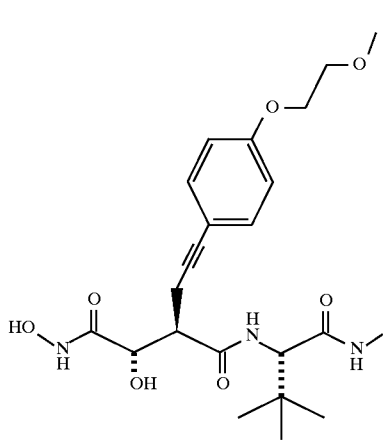

White solid. m.p. 185.4°–185.6° C. $^1$H-NMR; δ ((CD$_3$)$_2$SO), 10.65 (1H, s), 8.86 (1H, s), 7.89 (1H, m), 7.64 (1H, d, J=9.5 Hz), 7.24 (2H, d, J=8.6 Hz), 6.87 (2d, J =8.7 Hz), 5.57 (1H, d, J=7.6 Hz), 4.23 (1H, d, J=10.5 Hz), 4.08 (2H, t, J=4.3 Hz), 3.91 (1H, dd, J=7.8 Hz), 3.63 (2H, t, J=4.4 Hz), 3.29 (3H, s), 2.93 (1H, m), 2.40 (4H, m), 2.73 (1H, dd, J=5.3, 16.6 Hz), and 0.89 (9H, s). $^{13}$C-NMR; δ ((CD$_3$)$_2$SO), 170.8, 170.4, 168.4, 158.1, 132.8, 115.1, 114.4, 85.9, 81.3, 70.5, 70.3, 67.0, 59.8, 58.1, 49.8, 48.6, 34.4, 26.6 and 25.2. IR: ν$_{max}$, (KBr), 3319, 2954, 2883, 2367, 1637, 1566, 1508, 1367, 1249, 1120, 1061 and 832 cm$^{-1}$.

The starting material was prepared as follows:

To an ice-cooled solution of 4-bromophenoxyethanol (5 g, 23.0 mmol) in THF (30 ml) was added a suspension of sodium hydride (1.10 g, 46.1 mmol) in THF (30 ml), with stirring. After 20 minutes dimethyl sulfate (4.37 ml, 46.1 mmol) was added dropwise. The reaction mixture was stirred for 4 hours at room temperature then quenched slowly with saturated aq. ammonium chloride (50 ml). The mixture was extracted with ethyl acetate (100 ml) and the organic extract was washed successively with 1M hydrochloric acid (50 ml) and brine (50 ml), dried over anhydrous magnesium sulfate and filtered. The solvent was removed under reduced pressure to leave 4-(2-methoxy-ethoxy)-bromobenzene (5.5 g, ca. quant.) as a pale brown oil. $^1$H-NMR; δ (CDCl$_3$), 7.36 (2H, d, J=9.1 Hz), 6.80 (2H, d, J=9.1 Hz), 4.09 (2H, t, J=4.7 Hz), 3.74 (2H, t, J=4.7 Hz) and 3.45 (3H, s).

EXAMPLE 10

3R-[3-(4-Chloro-phenyl)-prop-2-ynyl]-2S,N¹-dihydroxy-N⁴-{1S-[2-(2-methoxy-ethylcarbamoyl]-2,2-dimethyl-propyl}-succinamide

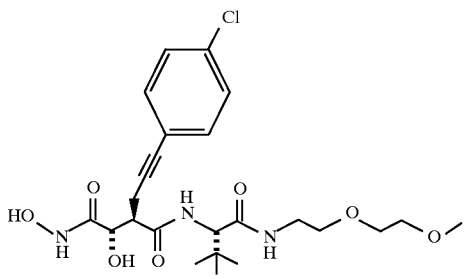

White solid. m.p. 69.2°–70.5° C. $^1$H-NMR; δ(CD$_3$OD), 8.25 (1H, m), 7.86 (1H, d, J=8.7 Hz), 7.19 (4H, dd, J=13.0, 8.7 Hz), 4.20 (1H, d, J=5.5 Hz), 4.14 (1H, d, J=8.8 Hz), 3.41 (8H, m), 3.25 (3H, s), 3.01 (1H, m), 2.73 (1H, dd, J=9.5, 16.9 Hz), 2.59 (1 H, dd, J =4.6, 16.9 Hz) and 0.88 (9H, s). $^{13}$C-NMR; δ (CD$_3$OD), 176.4, 175.2, 173.3, 137.2, 136.5, 131.9, 126.1, 91.6, 84.3, 75.4, 74.6, 73.3, 72.8, 65.2, 61.5, 52.8, 42.7, 37.7, 29.7 and 21.0.

EXAMPLE 11

3R-[3-(2-Chloro-phenyl)-prop-2-ynyl]-N⁴-(2,2-dimethyl-1 S-methylcarbamoyl-propyl)-2S, N¹-dihydroxy-succinamide

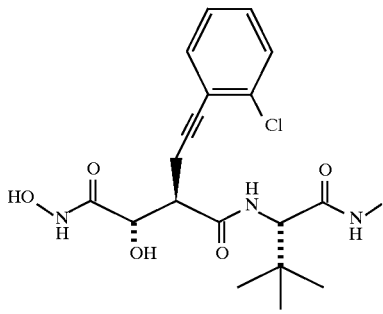

White solid. m.p. 179.3°–180° C. $^1$H-NMR; δ (CD$_3$OD), 8.03 (1H, m), 7.94 (1H, d, J =3.2 Hz), 7.45 (2H, m), 7.27 (2H, m), 4.36 (1H, d, J=5.8 Hz), 4.28 (1H, s), 3.15 (1H, m), 2.87 (1H, dd, J=8.2, 16.7 Hz), 2.77 (1H, dd, J=6.1, 16.7 Hz), 2.63 (3H, d, J=8.6 Hz) and 1.01 (9H, s). $^{13}$C-NMR; δ (CD$_3$OD), 172.6, 172.0, 170.2, 135.7, 133.7, 129.3, 129.1, 126.7, 123.4, 110.0, 92.0, 79.2, 71.2, 61.3, 49.1, 34.6, 26.2 and 25.0.

EXAMPLE 12

3R-[3-(4-Chloro-phenyl)-prop-2-ynyl]-N⁴-(1S-dimethylcarbamoyl-2,2-dimethyl-propyl)-2S, N¹-dihydroxy-succinamide

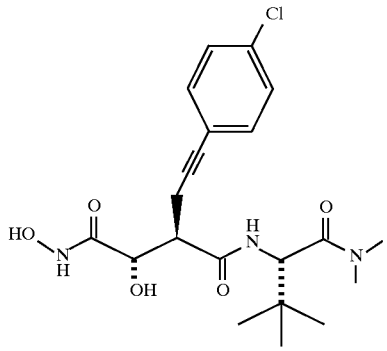

White solid. m.p. 104.5°–105.5° C. ¹H-NMR; δ (CD₃OD), 7.35 (4H, dd, J=11.4, 9.0 Hz), 4.96 (1H, s), 4.28 (1H, d, J=6.1 Hz), 3.16 (3H, s), 3.10 (1H, m), 2.82 (3H, s), 2.74 (2H, t, J=8.1 Hz) and 1.03 (9H, s). ¹³C-NMR; δ(CD₃OD), 172.8, 171.9, 170.2, 133.9, 133.2, 128.6, 122.5, 87.4, 81.3, 71.3, 65.9, 55.0, 49.2, 37.8, 35.6, 34.9 and 26.0.

EXAMPLE 13

N⁴-(2,2-Dimethyl-1S-methylcarbamoyl-propyl)-2S, N¹-dihydroxy-3R-(5-phenyl-penta-2, 4-diiynyl)-succinamide

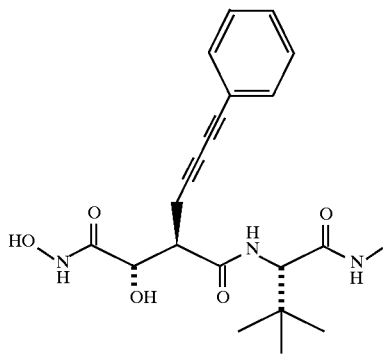

White solid. m.p. 198.8°–199.6° C. ¹H-NMR; δ (CD₃OD), 7.46 (2H, m), 7.38 (3H, m) ,4.29 (1H, d, J=5.6 Hz), 4.26 (1H, s), 3.10 (1H, m), 2.77 (2H, m), 2.74 (3H, s) and 1.03 (9H, s). ¹³C-NMR; δ(CD₃OD), 172.3, 172.1, 170.0, 132.4, 129.3, 128.6, 122.0, 80.6, 75.3, 73.8, 71.1, 66.8, 61.4, 48.7, 34.4, 26.4, 25.2 and 19.7. IR: $v_{max}$ (Kbr) 3309, 3236, 2963, 2872, 2364, 2330, 1634, 1525, 1369 and 1114 cm⁻¹.

The starting material was prepared as follows:

To a solution of sodium hypobromite [prepared by slow addition of bromine (11 ml) to 10M sodium hydroxide solution (50 ml) and crushed ice (100 g)] was added a solution of phenylacetylene (20.4 g, 19.97 mmol) in THF (10 ml). The two phase mixture was stirred vigorously for 5 hours. Saturated aq. ammonium chloride was added and the mixture was extracted with diethyl ether (3×30 ml). The combined organic extracts were washed with brine, dried over anhydrous magnesium sulfate and filtered. The solvent was removed under reduced pressure to provide 1-bromo-2-phenyl-acetylene (36.2 g, 99%) as a yellow oil. ¹H-NMR; δ (CDCl₃), 7.50 (m). IR: $V_{max}$ (neat) 2200 cm⁻¹.

EXAMPLE 14

N⁴-(1S-benzyl-2-hydroxy-ethyl)-3R-[3-(4-Chloro-phenyl)-prop-2-ynyl]-2S, N¹-dihydroxy-succinamide

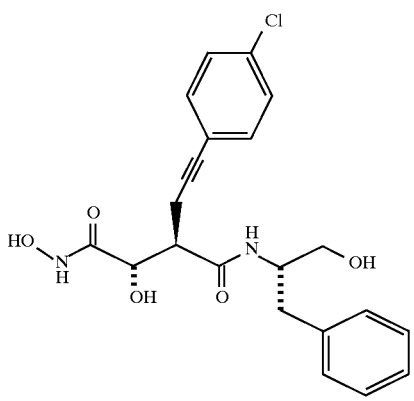

White solid. m.p. 137.2°–137.4° C. ¹H-NMR; δ(CD₃OD), 7.16 (9H, m), 4.19 (1H, d, J=5.4 Hz), 3.99 (1H, m), 3.39 (2H, m), 2.83 (1H, m), 2.75 (2H, t, J=7.1 Hz) and 2.58 (2H, d, J=7.7 Hz). ¹³C-NMR; δ (CD₃OD), 174.3, 171.8, 140.1, 135.3, 134.5, 130.9, 130.0, 129.8, 127.8, 124.0, 89.0, 82.7, 72.5, 63.9, 54.7, 50.6, 38.3 and 20.8. IR: $v_{max}$ (KBr), 3528, 3277, 3201, 2940, 1643, 1559, 1488, 1088 and 1022 cm⁻¹.

EXAMPLE 15

2,N¹-Dihydroxy-N⁴-(1-hydroxymethyl-3-methyl-butyl)-3R-(5-phenyl-penta-2, 4,diynyl)-succinamide

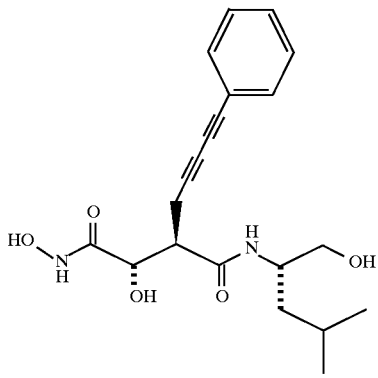

Pale yellow solid. m.p. 134.4°–134.6° C. ¹H-NMR; δ(CD₃OD), 7.37 (2H, m), 7.26 (3H, m), 4.10 (1H, d, J=5.9Hz), 3.90 (1H, m), 3.49 (1H, dd, J=5.3, 11.0Hz), 3.34 (1H, m), 2.82 (1H, m), 2.60 (2H, dd, J=5.9, 8.0 Hz), 1.65 (1H, m), 1.30 (2H, m) and 0.82 (6H, t, J=6.6 Hz). ¹³C-NMR; δ(CD₃OD), 173.9, 171.6, 133.9, 130.7, 130.0, 123.4, 82.2, 76.7, 75.1, 72.6, 68.7, 67.3, 51.2, 50.4, 41.5, 26.1, 24.4, 22.6 and 20.9.

We claim:
1. A compound of formula (I)

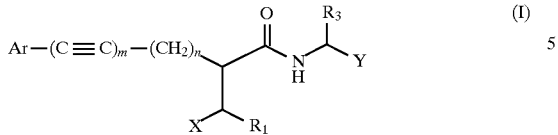

wherein
Ar represents an optionally substituted phenyl or heteroaryl group;
m is 1 or 2;
n is 0, 1, 2, 3 or 4;
x represents —COOH or —CONHOH;
$R_1$ represents hydrogen, $(C_1–C_6)$alkyl; $(C_3–C_8)$ cycloalkyl; $(C_2–C_6)$alkenyl; phenyl; substituted phenyl; phenyl $(C_1–C_6)$alkyl); substituted phenyl$(C_1–C_6)$ alkyl; heterocyclyl; substituted heterocyclyl; heterocyclyl$(C_1–C_6)$alkyl; substituted heterocyclyl $(C_1–C_6)$alkyl; amino; protected amino; acylamino; OH; SH; $(C_1–C_6)$ alkoxy; $(C_1–C_6)$alkylamino; di-$(C_1–C_6)$ alkylamino; $(C_1–C_6)$alkylthio; amino $(C_1–C_6)$alkyl; hydroxy$(C_1–C_6)$alkyl, mercapto$(C_1–C_6)$alkyl or carboxy$(C_1–C_6)$ alkyl wherein the amino-, hydroxy-, mercapto- or carboxyl-group are optionally protected or the carboxyl- group amidated; lower alkyl substituted by carbamoyl, mono(lower alkyl)carbamoyl, di(lower alkyl)carbamoyl, di(lower alkyl)amino, or carboxy-lower alkanoylamino; or a group B'SO$_p$A'— wherein p is 0, 1 or 2 and B' is hydrogen or a $(C_1–C_6)$ alkyl, phenyl, substituted phenyl, heterocyclyl, $(C_1–C_6)$ acyl, phenacyl or substituted phenacyl group, and A' represents $(C_1–C_6)$alkyl;
$R_3$ represents the characterising group of a natural or non-natural α amino acid in which any functional groups may be protected;
Y Is a group of formula (ID) or (IE)

wherein:
R4 represents
(a) an optionally substituted cycloalkyl or cycloalkenyl ring; or
(b) a phenyl or heteroaryl ring which may be fused to a benzene or heteroaryl ring, either or both of which rings may be substituted, and in which any ring nitrogen atom may be oxidised as an N-oxide, or
(c) a group —CHR$^x$R$^y$ wherein R$^x$ and R$^y$ each independently represents an optionally substituted phenyl or heteroaryl ring which may be linked covalently to each other by a bond or by a $C_1–C_4$ alkylene or $C_2–C_4$ alkenylene bridge;
(d) a group of formula —(Z'—O)$_w$—Z wherein Z' is straight or branched $C_1–C_6$ alkyl optionally interrupted by one or more non-adjacent S and/or N atoms, w is an integer >1, and no continuous linear sequence of atoms in the group $R_4$ is >12, or
(e) a straight or branched $C_1–C_6$ alkyl group, optionally interrupted by one or more non-adjacent S and/or N atoms, which is substituted by at least two substituents of formula —(Z''')$_x$—(OZ)$_q$ wherein Z''' is straight or branched $C_1–C_6$ alkyl optionally interrupted by one or more non-adjacent S and/or N atoms, x is 0 or 1, q is 1 or 2, and no continuous linear sequence of atoms in the group $R_4$ is >12, or
(f) hydrogen, $C_1–C_6$ alkyl, $C_1–C_4$ perfluoroalkyl, or a group D-($C_1–C_6$ alkyl)- wherein D is hydroxy, $C_1–C_6$ alkoxy, $C_1–C_6$ alkylthio, acylamino, optionally substituted phenyl or heteroaryl, NH$_2$, or mono- or di-($C_1–C_6$ alkyl)amino or N-morpholino;
or $R_3$ and $R_4$ taken together represent a divalent chain of formula -C(R$^a$)(R$^b$)-A''-Alk-wherein R$^a$ and R$_b$ are independently hydrogen or $C_1–C_6$ alkyl, A'' is a bond, —O—, —S—, —S—S—, —NH— or —NRa— wherein R$^a$ is $C_1–C_6$ alkyl, and Alk is $C_1–C_6$ alkylene; and
$R_5$ is hydrogen or a $C_1–C_6$ alkyl group;
$R_6$ is hydrogen, $C_1–C_6$ alkyl, phenyl($C_1–C_6$ alkyl) or heterocyclyl($C_1–C_6$ alkyl);
$R_7$ is hydrogen or a $C_1–C_6$ alkyl group;
or (when $R_7$ is hydrogen) $R_3$ and $R_7$ taken together with the carbon atoms to which they are attached form a 2-hydroxycyclohexyl or $C_6$ sugar (hexose) ring;
or $R_6$ and $R_7$ taken together with the carbon atom to which they are attached form a 5 or 6-membered carbocyclic or heterocyclic ring;
and salts hydrates and solvates thereof.

2. A compound as claimed in claim 1 wherein the stereochemistry is as follows:
C atom carrying the groups X and $R_1$—S,
C atom carrying the triple unsaturated group —R,
C atom carrying the groups $R_3$ and Y—S.

3. A compound as claimed in claim 1 or claim 2 wherein n is 0 or 1.

4. A compound as claimed in claim 1 or claim 2 wherein Ar is a phenyl group which is substituted in the 4-position by a phenyl, phenoxy, phenylthio, heteroaryl (eg 2-, 3- or 4-pyridyl), heteroaryloxy (eg 2-, 3- or 4-pyridyloxy) or heteroarylthio ((eg 2-, 3- or 4- pyridylthio) group which in turn is optionally substituted by $C_1–C_6$ alkyl, $C_1–C_6$ alkoxy ($C_1–C_6$ alkoxy), phenoxy, phenylthio, trifluoromethyl, halo, cyano (—CN), —CH$_2$CN, —OH, or —OR, wherein R is $C_1–C_6$ alkyl or benzyl.

5. A compound as claimed in claim 1 or claim 2 wherein Ar is a phenyl group which is optionally substituted by $C_1–C_6$ alkyl eg methyl, ethyl, n-propyl, n-butyl, n-pentyl and n-hexyl; $C_1–C_6$ alkoxy($C_1–C_6$ alkoxy), 2-methoxyethoxy, phenoxy, phenylthio, trifluoromethyl, halo, cyano (—CN), —CH$_2$CN, —OH, or —OR, wherein R is $C_1–C_6$ alkyl or benzyl.

6. A compound as claimed in claim 1 or claim 2 wherein Ar is a phenyl group optionally substituted in the 4 position by 2-methoxyethoxy, trifluoromethyl, chloro, methoxy, cyano, or 2-methoxyethoxy.

7. A compound as claimed in claim 1 or claim 2 wherein Ar is a biphenyl group optionally substituted in the 4' position by 2-methoxyethoxy, trifluoromethyl, chloro, methoxy, cyano, or 2-methoxyethoxy.

8. A compound as claimed in claims 1 and 2 wherein $R_1$ is hydrogen, $C_1–C_4$ alkyl, cyclopentyl, hydroxy, methoxy, allyl, or a group —(CH$_2$)$_t$—W wherein t represents 1, 2, 3 or 4 and W represents phthalimido, 1,2-dimethyl-3,5-dioxo-1,2,4-triazolidin4-yl, 3,4,4-trimethyl-2,5-dioxo-1-imidazolidinyl 2-methyl-3,5-dioxo-1,2,4-oxadiazol-4-yl, 3-methyl-2,4,5-trioxo-1-imidazolidinyl, 2,5-dioxo-3- phenyl-1-imidazolidinyl-2-oxo-1-pyrrolidinyl, 2,5-dioxo-1-pyrrolidinyl, 2,6-dioxopiperidinylnaphththalimido (ie 1,3-dihydro-1,3-dioxo-2H-benz [f]isoindol-2-yl, 1,3-dihydro-1-oxo-2H-benz[f]isoindol-2-yl, 1,3-dihydro-1,3-dioxo-2H-pyrrolo[3,4-b]quinolin-2-yl, 2,3-dihydro-1,3-dioxo-1H-benz[d,e]isoquinolin-2-yl or saccharinyl.

9. A compound as claimed in claims 1 and 2 wherein $R_3$ is methyl, benzyl, 4-chlorophenylmethyl, 2-thienylmet t-butyl, 1 -benzylthio-1 -methylethyl, 1 -mercapto-1 methylethyl or 3H-imidazol-4yl-methyl.

10. A compound as claimed in claims 1 and 2 wherein Y is a group of formula (ID) and $R_4$ is cyclopropyl, cyclobutyl, cyclopentyl, cyclohexyl cycloheptyl or cyclooctyl; phenyl, 2-methyoxyphenyl, 3-methoxyphenyl, 4-methoxyphenyl, 3,4-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2-t-butylphenyl, 3-t-butylpyhenyl, 4-t-butylphenyl, 4-t-butyl-2, 6-dimethylphenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulphonylphenyl, 3-methylsulphonylphenyl, 4-methylsulphonylphenyl, 2-trifluoromethylphenyl,3-trifluoromethylphenyl, 4-trifluoromethylphenyl, 3,5-ditrifluoromethylphenyl,2-trifluoromethylphenyl,3-aminophenyl, 4-aminophenyl,2N,N-dimethylaminophenyl,3-N,N-dimethylaminophenyl, 4-N,N-dimethylaminophenyl,2hydroxyphenyl,3-hydroxyphenyl, 4-hydroxyphenyl, 2-napthyl, furan-2-yl, thien-2-yl, pyrrol-2-yl, tetrahydrofuran-2-yl, imidazol-2-yl, thiazol-2-yl, 4-ethoxycarbonylmethylthiazol-2-yl, 4-phenylthiazol-2-yl, 4,5-dimethylthiazol-2-yl, 5-bromothiazol-2-yl, 4-tert-butylthiazol-2-yl, benzothiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2yl,5-methyl-1,3,4-thiadiazol-2-yl, pyridin-2-yl, pyridin-3-yl, pyridin-4-yl, N-oxides of pyridin-2-yl pyridin-3-yl and pyridin-4-yl, piperazin-1-yl, indol-2-yl, benzimidazol-2-yl, benzotriazol-2-yl, pyrazin-2-yl, 1,2-pyridazin-3-yl, 1,3-pyrimidin-5-yl, 1,3-dithian-2-yl, benzo[b]thien-2-yl, isoxazol-5-yl, or quinolin-3-yl;

a group —CHR$^x$R$^y$ wherein R$^x$ and R$^y$ independently represent optionally substituted phenyl, thienyl, furyl, pyrrolyl, imidazolyl, thiazolyl, pyrazolyl, isoxazolyl, isothiazolyl, triazolyl, thiadiazolyl, oxadiazolyl, pyridinyl, pyridazinolyl, pyrimidinyl, piperazinyl or triazinyl;

a polyether chain possessing at least two non-adjacent oxygen atoms, for example 2-(2-methoxyethoxymethoxy)ethyl, 1,1 -dimethyl-2-(2-methoxyethoxymethoxy)ethyl, 2-(2-ethoxyethoxymethoxy)ethyl, 2-(2-(2-methoxyethoxy)ethoxy)ethyl, 2-(2-(3-methoxypropoxymethoxy)ethyl, 3-(2-methoxyethoxymethoxy)

propyl, 2,2-dimethyl-3-(2-methoxyethoxymethoxy) propyl, 2-(2-methoxyethoxy)ethyl, 3-(2-methoxyethoxy)propyl, 2-methyl-2,2-di(2-methoxyethyl)propyl, 2-methyl-2,2-di(2-methoxyethyl)propyl, 2-methyl-2,2-di (2-methoxyethyl)butyl, and 2-methyl-2,2-di(2-methoxymethyl)propyl;

methyl, ethyl, n- or iso-propyl, n-, sec- or tert-butyl, hydroxyethyl, hydroxypropyl, 2,2-dimethyl-3-hydroxypropyl, hydroxybutyl, methoxyethyl, ethoxyethyl, methoxypropyl, 2,2-dimethyl-3-methoxypropyl, 2,2-dimethyl-3-ethoxypropyl, 2-ethylthioethyl, 2-acetoxyethyl, N-acetyl-aminoethyl, 3-(2-pyrrolidone) propyl, morpholin-4-ylpropyl, optionally substituted phenylethyl, phenylpropyl, phenylbutyl, or phenylpentyl.

11. A compound as claimed in claim 10 wherein Y is a group of formula (ID) and $R_5$ is hydrogen, methyl or ethyl.

12. A compound as claimed in claim 10 wherein Y is a group of formula (ID), $R_4$ is hydrogen or methyl and $R_5$ is methyl.

13. A compound as claimed in claim 10 wherein Y is a group of formula (IE) and $R_6$ is hydrogen, methyl, ethyl, benzyl or pyridylmethyl.

14. A compound as claimed in claim 10 wherein Y is a group of formula (IE) and $R_7$ is hydrogen or methyl.

15. A compound as claimed in claim 10 wherein Y is a group of formula (IE), and $R_6$ and $R_7$ are each hydrogen.

16. A compound as claimed in claim 10 wherein Y is a group of formula (IE) and $R_6$ and $R_7$ taken together with the carbon atom to which they are attached form a cyclopentyl, cyclohexyl or morpholino ring.

17. A compound as claimed in claim 1 or claim 2 wherein Ar is phenyl or substituted phenyl;
m is 1 or 2;
n is 1;
X is —CONHOH,
$R_1$ is hydrogen, $C_1$—$C_4$alkyl, cyclopentyl, hydroxy, methoxy, allyl, or a group —(CH$_2$)$_t$-W wherein t represents 1, 2, 3 or 4 and W represents phthalimido, 1,2-dimethyl-3,5-dioxo-1,2,4-triazolidin-4-yl, 3,4,4-trimethyl-2,5-dioxo-1 -imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl-2-oxo-1-pyrrolidinyl, 2,5-dioxo-1 -pyrrolidinyl or 2,6-dioxo-piperidinylnaphththalimido (ie 1 ,3-dihydro-1,3-dioxo-2H-benz[f]isoindol-2-yl), 1,3-dihydro-1-oxo-2H-benz[flisoindol-2-yl, 1,3-dihydro-1,3-dioxo-2H-pyrrolo[3,4-b] quinolin-2-yl, 2,3-dihydro-1,3-dioxo-1H-benz[d,e]isoquinolin-2-yl or saccharinyl;

$R_3$ is t-butyl, 1-benzylthio-1-methylethyl, 1-mercapto-1-methylethyl, benzyl, methyl, or 3H-imidazol-4-ylmethyl;

Y is a group of formula (ID) wherein $R_4$ represents cyclopropyl, cyclobutyl, cyclopentyl, cyclohexyl, cycloheptyl or cyclooctyl;
phenyl, 3-methoxyphenyl, pyridin-2-yl, pyridin-3-yl, thiazol-2-yl, 4-ethoxycarbonylmethylthiazol-2-yl, 5-methyl-1,3,4-thiadiazol-2-yl or 4-tert-butylthiazol-2-yl;
a group —CHR$^x$R$^y$ wherein R$^x$ and R$^y$ independently represent phenyl or 4-chlorophenyl or R$^x$ and R$^y$ are linked covalently in a 9-H-fluoren-9-yl ring;
a polyether chain possessing at least two non-adjacent oxygen atoms, for example 2-(2-methoxyethoxy) ethyl; or
hydrogen, methyl or 3-morpholin-4-ylpropyl;
or $R_3$ and $R_4$ taken together represent —C(CH$_3$) $_2$SCH$_2$CH$_2$CH$_2$-, or —C(CH$_3$)$_2$SSCH $_2$ CH$_2$-;and
$R_5$ represents hydrogen or methyl;
or Y is a group of formula (IE) wherein $R_6$ and $R_7$ are both hydrogen.

18. A compound as claimed in claim 17 wherein Ar is 4-phenyl-phenyl, 4-phenoxy-phenyl, 4-(4'-chlorophenyl)-phenyl, 4-(4-cyanophenyl)-phenyl, 4-(4'-methoxy)-phenyl, 4-[4'-(2-methoxyethoxy)phenyl]-phenyl, 4-(pyridin-4-yl)-phenyl, 4-(pyridin-4-yloxy)-phenyl, 4-(4'-bromophenyl)-phenyl, 4-trifluoromethyl-phenyl, 4-fluorophenyl, 4-methoxyphenyl, 4-methoxyethoxyphenyl, 4-propylphenyl, 4-methylphenyl or 4-chlorophenyl.

19. A compound selected from the group consisting of 3R-(3-biphenyl-4-yl-prop-2-ynyl)-$N^4$-(2,2-dimethyl-1S-methylcarbamoyl-propyl)-2S, $N^1$-dihydroxy-succinamide;

$N^4$-(2,2-dimethyl-1S-methylcarbamoyl-propyl)-2S, $N^1$-dihydroxy-3R-(3-phenyl-prop-2-ynyl)-succinamide;

$N^4$-(2,2-dimethyl-1S-methylcarbamoyl-propyl)-2S, $N^1$-dihydroxy-3R-(3-[4-trifluoromethyl-phenyl-prop-2-ynyl)-succinamide;

3R-[3-(4-chloro-phenyl)-prop-2-ynyl]-$N^4$-(2,2-dimethyl-1S-methylcarbamoyl-propyl)-2S, $N^1$-dihydroxy-succinamide;

$N^4$-(2,2-dimethyl-1S-methylcarbamoyl-propyl)-2S,$N^1$-dihydroxy-3R-[3-(4-methoxy-phenyl)-prop2-ynyl]-succinamide, 3R-[3-(4'-chloro-biphenyl-4-yl )-prop-2-ynyl]-$N^4$-(2,2-dimethyl-1S-methylcarbamoyl-propyl)-2S,$N^1$-dihydroxy-succinamide, 3R-[3-(4-cyanophenyl)-prop-2-ynyl]-$N^4$-(2,2-dimethyl-1S-methylcarbamoyl-propyl)-2S, $N^1$-dihydroxy-succinamide, 3R-[3-(4-chloro-phenyl)-prop-2-ynyl]-$N^4$-[2,2-dimethyl-1S-(3-morpholin-4-yl-propylcarbamoyl)-propyl]-2S, $N^1$-dihydroxy-succinamide, $N^4$-(2,2-dimethyl-1S-methylcarbamoyl-propyl)-2S,$N^1$-dihydroxy-3-{3-[4-(2-methoxy-ethoxy)-phenyl]-prop-2-ynyl}-succinamide, 3R-[3-(4-chloro-phenyl)-prop-2-ynyl]-2S,$N^1$-dihydroxy-$N^4$-{1S-[2-(2-methoxy-ethoxy)-ethylcarbamoyl]-2,2-dimethyl-propyl}-succinamide, 3R-[3-(2-chloro-phenyl )-prop-2-ynyl]-$N^4$-(2,2-dimethyl-1 S-methylcarbamoyl-propyl)-2S, $N^1$-dihydroxy-succinamide, 3R-[3-(4-chloro-phenyl)-prop-2-ynyl]-$N^4$-(1S-dimethylcarbamoyl-2,2-dimethyl-propyl)-2S, $N^1$-dihydroxy-succinamide, $N^4$-(2,2-dimethyl-1S-methylcarbamoyl-propyl)-2S,$N^1$-dihydroxy-3R-(5-phenyl-penta-2,4-diynyl)-succinamide, $N^4$-(1S-benzyl-2-hydroxy-ethyl)-3R-[3-(4-Chloro-phenyl)-prop-2-ynyl]-2S,$N^1$-dihydroxy-succinamide, 2,$N^1$-dihydroxy-$N^4$-(1-hydroxymethyl-3-methyl-butyl)-3R-(5-phenyl-penta- 2,4,diynyl)-succinamide, and salts, hydrates and solvates thereof.

20. A compound selected from the group consisting of $N^4$-(1S-dimethylcarbamoyl-2,2-dimethyl-propyl)-2S,$N^1$-dihydroxy-3R-[3-( 4-methoxy-phenyl)-prop-2-ynyl]-succinamide, 3R-(3-biphenyl-4-yl-prop-2-ynyl)-$N^4$-(1S-dimethylcarbamoyl-2,2-dimethyl-propyl)-2S, $N^1$-dihydroxy-succinamide, 3R-[3-(4'-chloro-biphenyl-4-yl)-prop-2-ynyl]-$N^4$-(1S-dimethylcarbamoyl-2,2-dimethyl-propyl)-2S,$N^1$-dihydroxy-succinamide, 3R-[3-(4-chloro-phenyl )-prop-2-ynyl]-2S,$N^1$-dihydroxy-$N^4$-( 1S-hydroxymethyl-2,2-dimethyl-propyl)-succinamide, 3R-[3-(4-chloro-phenyl)-prop-2-ynyl]-2S,$N^1$-dihydroxy-$N^4$-[2-hydroxy-1-(3H-imidazol-4-ylmethyl)-ethyl]-succinamide, 3R-[3-(4'-chloro-biphenyl-4-yl)-prop-2-ynyl]-2S,$N^1$-dihydroxy-$N^4$-(2-hydroxy-1S-methyl-ethyl)-succinamide, $N^4$-(1S-benzyl-2-hydroxy-ethyl)-3R-(3-biphenyl-4-yl-prop-2-ynyl)-2S,$N^1$-dihydroxy-succinamide, 3R-[3-(4-chloro-phenyl)-prop-2-ynyl]-$N^4$-(1S-dimethylcarbamoyl-2,2-dimethyl-propyl)-$N^1$-hydroxy-succinamide, $N^4$-(2-benzylsulfanyl-1S-dimethylcarbamoyl-2-methyl-propyl)-3R-[3-(4-chloro-phenyl)-prop-2-ynyl]-2S,$N^1$-dihydroxy-succinamide, 3R-[3-(4-chloro-phenyl)-prop-2-ynyl]-$N^4$-(2,2-dimethyl-1S-methylcarbamoyl-propyl)-$N^1$-hydroxy-2S-methoxy-succinamide and salts, hydrates and solvated thereof.

21. A pharmaceutical composition comprising a compound as claimed in claims 1,2,19 or 20, together with a pharmaceutically or veterinarily acceptable carrier.

22. A pharmaceutical composition comprising a compound as claimed in claim 17, together with a pharmaceutically or veterinarily acceptable carrier.

23. A pharmaceutical composition comprising a compound as claimed in claim 18, together with a pharmaceutically or veterinarily acceptable carrier.

24. A pharmaceutical composition comprising a compound as claimed in claim 19, together with a pharmaceutically or veterinarily acceptable carrier.

* * * * *